US010041876B2

(12) United States Patent
Nishihara et al.

(10) Patent No.: US 10,041,876 B2
(45) Date of Patent: Aug. 7, 2018

(54) PHOTOACOUSTIC MEASUREMENT APPARATUS

(75) Inventors: Hiroshi Nishihara, Kawasaki (JP);
Kazuhiko Fukutani, Yokohama (JP);
Takao Nakajima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 682 days.

(21) Appl. No.: 13/003,503

(22) PCT Filed: Jul. 9, 2009

(86) PCT No.: PCT/JP2009/062846
§ 371 (c)(1),
(2), (4) Date: Jan. 10, 2011

(87) PCT Pub. No.: WO2010/005109
PCT Pub. Date: Jan. 14, 2010

(65) Prior Publication Data
US 2011/0112391 A1 May 12, 2011

(30) Foreign Application Priority Data

Jul. 11, 2008 (JP) ................................. 2008-182060

(51) Int. Cl.
*A61B 5/05* (2006.01)
*G01N 21/17* (2006.01)
(Continued)

(52) U.S. Cl.
CPC ....... *G01N 21/1702* (2013.01); *A61B 5/0059* (2013.01); *A61B 5/0095* (2013.01);
(Continued)

(58) Field of Classification Search
CPC ... A61B 5/0059; A61B 5/0091; A61B 5/0095; A61B 5/14546; A61B 5/4312
See application file for complete search history.

(56) References Cited

U.S. PATENT DOCUMENTS 5,293,873 A    3/1994  Fang
5,787,887 A *  8/1998  Klingenbeck-Regn ....... 600/407
(Continued)

FOREIGN PATENT DOCUMENTS

EP    1493380 A    1/2005
EP    2036487 A    3/2009
(Continued)

OTHER PUBLICATIONS

Karabutov et al., "Optoacoustic images of early cancer in forward and backward modes." Proceedings of SPIE vol. 4434 (2001). pp. 13-27.*

(Continued)

*Primary Examiner* — James Kish
(74) *Attorney, Agent, or Firm* — Canon USA Inc., IP Division

(57) ABSTRACT

A measurement apparatus capable of measuring a position and a size of an absorber with high accuracy, which includes: a light source unit for emitting a pulse beam; an illumination optical unit for leading the pulse beam emitted by the light source unit to an inside of an inspection object; and an acoustic signal detection unit for detecting a photoacoustic signal generated by the pulse beam in which the illumination optical unit includes a first and second illumination optical units that are arranged so that the inspection object is irradiated with the pulse beam from both sides thereof opposingly; and the acoustic signal detection unit is provided so that a detection surface of the acoustic signal detection unit is positioned on the same side as that of one of irradiation surfaces of the inspection object which the first and second illumination optical units irradiate with the pulse beam.

20 Claims, 14 Drawing Sheets

(51) Int. Cl.
 *A61B 5/00* (2006.01)
 *A61B 5/145* (2006.01)
(52) U.S. Cl.
 CPC ........ *A61B 5/14546* (2013.01); *A61B 5/4312* (2013.01); *A61B 5/0091* (2013.01); *G01N 2021/1706* (2013.01)

(56) References Cited

U.S. PATENT DOCUMENTS

| | | | |
|---|---|---|---|
| 5,840,023 A | 11/1998 | Oraevsky et al. | |
| 7,898,649 B2* | 3/2011 | Masumura | 356/73 |
| 2002/0193678 A1* | 12/2002 | Kruger | A61B 5/0095 600/407 |
| 2003/0167002 A1 | 9/2003 | Nagar et al. | |
| 2004/0127783 A1 | 7/2004 | Kruger | |
| 2005/0107694 A1* | 5/2005 | Jansen | A61B 5/0091 600/431 |
| 2008/0123083 A1 | 5/2008 | Wang et al. | |
| 2008/0242979 A1* | 10/2008 | Fisher et al. | 600/427 |
| 2008/0306371 A1* | 12/2008 | Fukutani | A61B 5/0059 600/407 |
| 2009/0005685 A1* | 1/2009 | Nagae | A61B 5/0059 600/459 |

FOREIGN PATENT DOCUMENTS

| | | | |
|---|---|---|---|
| JP | 2005-021380 A | 1/2005 | |
| JP | 2007259915 A | 10/2007 | |
| WO | WO 2007/047114 | * 4/2007 | ............... A61B 6/03 |

OTHER PUBLICATIONS

Russian Office Action related to Application No. 2011105013/14 with English Translation dated May 6, 2012; six (6) pages in total.
The International Preliminary Report on Patentability (Chapter I of the Patent Cooperation Treaty) issued in international application No. PCT/JP2009/062846. 9 pages enclosed.
Manohar et al., "The Twente Photoacoustic Mammoscope: System Overview and Performance", Physics in Medicine and Biology, Institute of Physics Publishing, May 18, 2005, pp. 2543-2557.

* cited by examiner

PHOTOACOUSTIC MEASUREMENT APPARATUS

CROSS REFERENCE TO RELATED APPLICATIONS

This application is a U.S. National Stage of International application No. PCT/JP2009/062846 filed on Jul. 9, 2009 which claims priority from Japanese Patent Application No. JP2008-182060 filed on Jul. 11, 2008, the disclosures of which are hereby incorporated by reference herein in their entirety.

TECHNICAL FIELD

The present invention relates to a measurement apparatus for measuring spectral characteristics of the inside of a biological tissue. In particular, the present invention is applicable to a measuring apparatus that utilizes a photoacoustic effect.

BACKGROUND ART

The measurement apparatus for measuring spectral characteristics of the inside of a biological tissue is used for determining formation of new blood vessels or oxygen metabolism of hemoglobin attending on growth of tumor based on light absorption characteristics of a specific substance such as hemoglobin contained in blood, to thereby utilize the results for diagnosis.

Such an apparatus uses a near infrared beam having a wavelength of approximately 600 to 1,500 nm with excellent transmittance property for a biological tissue.

As a method of measuring spectral characteristics of the inside of a biological tissue, there is known a method utilizing a photoacoustic effect. An apparatus using this method irradiates the interior of a biological tissue with a pulse beam so that spectral characteristics of a local region can be measured from a photoacoustic signal that is generated based on light energy.

Intensity of the light applied to the interior of the biological tissue is attenuated by absorption and dispersion during the process of propagating in the biological tissue, and thus little light reaches a deep part of the tissue.

Conventionally, in order to solve those problems, there is proposed an apparatus in which two illumination optical systems are disposed at positions that are opposed to each other with respect to an inspection object, and the inspection object is illuminated from both sides thereof so that increased light can reach the deep part (see U.S. Patent application No. 2004/0127783).

In addition, there is proposed an apparatus in which optical fibers for irradiating the biological tissue with light and piezoelectric elements for detecting the photoacoustic signal are arranged alternately, or transparent piezoelectric elements through which light for irradiation can pass are used, whereby a detector for the photoacoustic signal is disposed on the same side as that of the illumination optical system (see Japanese Patent Application Laid-Open No. 2005-021380).

Further, there is proposed an apparatus in which a transducer for detecting a photoacoustic signal is disposed on the same side as that of the optical fiber for irradiating a biological tissue with light, and these are scan-driven along the surface of an inspection object (see U.S. Pat. No. 5,840,023).

Further, there is proposed an apparatus in which an inspection object such as a breast is pressed to be flat, and a plane for irradiating the flat inspection object with light is switched (see "The Twente Photoacoustic Mammoscope: system overview and performance" Phys. Med. Biol. 50 (2005), pp. 2543-2557).

However, the conventional measurement apparatus for measuring spectral characteristics of the inside of a biological tissue has a following problem. The light propagating inside the biological tissue is affected by an anisotropy parameter g. The anisotropy parameter g has a value of approximately 0.9 in a biological tissue and mainly causes forward scattering.

On this occasion, energy of the light that is absorbed by an absorber in the biological tissue becomes larger in a position closer to the light incidence side due to an influence of the forward scattering.

As to a photoacoustic wave that is a photoacoustic signal generated from the absorber having a biased distribution of the energy of the absorbed light as described above, the signal generated from a boundary in the light incidence direction in which the energy of the absorbed light is large has the largest intensity.

In the structure described in U.S. Patent Application No. 2004/0127783, the transducer for detecting the photoacoustic signal is disposed on a plane different from that of the two illumination optical systems. In other words, the transducer is not disposed in the light incidence direction.

In a case where a photoacoustic signal generated from a spherical absorber is detected with the structure described above, a signal generated from a boundary at a position closest to the transducer is received first, and a signal generated from a boundary of the absorber at a position farthest from the transducer is received last.

From such a signal profile, the time for propagating in the spherical absorber and the sonic speed in the biological tissue are read, whereby the position and the size of the absorber can be calculated.

However, the position closest to the transducer and the position farthest from the transducer are in a direction different from the light incidence direction, and hence the propagation time cannot be detected with the signal of the largest intensity as described above.

In addition, according to Japanese Patent Application Laid-Open No. 2005-021380 and U.S. Pat. No. 5,840,023, the illumination optical system and the transducer for detecting the photoacoustic signal are disposed on the same plane, but the illumination optical system is disposed on only one plane.

With this structure, energy of light absorbed by the absorber becomes large on the light incidence side and becomes small on the opposite side thereto.

Therefore, the signal generated from the boundary at the position closest to the transducer can be detected with the largest intensity, but the signal generated from the boundary at the position farthest from the transducer cannot be detected with the largest intensity. Further, according to "The Twente Photoacoustic Mammoscope: system overview and performance" Phys. Med. Biol. 50 (2005), pp. 2543-2557, a pressed inspection object is illuminated on the both sides thereof one side by one side, but a time delay occurs because the illumination direction is switched.

With this structure, energies of light entering from both sides are not superimposed on each other, and thus the amount of light reaching the deep part of the tissue cannot be increased.

Therefore, intensity of a photoacoustic signal generated from the absorber in a deep part of the tissue becomes small. As described above, even if any one of the technologies described as conventional examples is used, there is a problem in detecting a position and a size of an absorber positioned in a deep part of a biological tissue with high accuracy and high contrast.

DISCLOSURE OF THE INVENTION

The present invention has been made in view of the above-mentioned problem, and therefore an object thereof is to provide a measurement apparatus capable of measuring a position and a size of an absorber accurately by detecting a photoacoustic signal generated from a boundary of the absorber positioned in a deep part of a biological tissue with a high contrast signal.

The present invention aims to provide a measurement apparatus having the following structure.

The measurement apparatus of the present invention comprises: a light source unit for emitting a pulse beam; an illumination optical unit for leading the pulse beam emitted by the light source unit to an inside of an inspection object; and an acoustic signal detection unit for detecting a photoacoustic signal generated by the pulse beam led to the inside of the inspection object, wherein the illumination optical unit includes a first illumination optical unit and a second illumination optical unit that are arranged so that the inspection object is irradiated with the pulse beam from both sides thereof opposingly; and the acoustic signal detection unit is disposed so that a detection surface of the acoustic signal detection unit is positioned on the same side as that of one of irradiation surfaces of the inspection object which the first illumination optical unit and the second illumination optical unit irradiate with the pulse beam.

It is possible to realize a measurement apparatus capable of measuring a position and a size of an absorber with high accuracy by detecting a photoacoustic signal generated from a boundary of the absorber positioned in a deep part of a biological tissue with a high contrast signal.

Further features of the present invention will become apparent from the following description of exemplary embodiments with reference to the attached drawings.

BEST MODE FOR CARRYING OUT THE INVENTION

Figure 1:
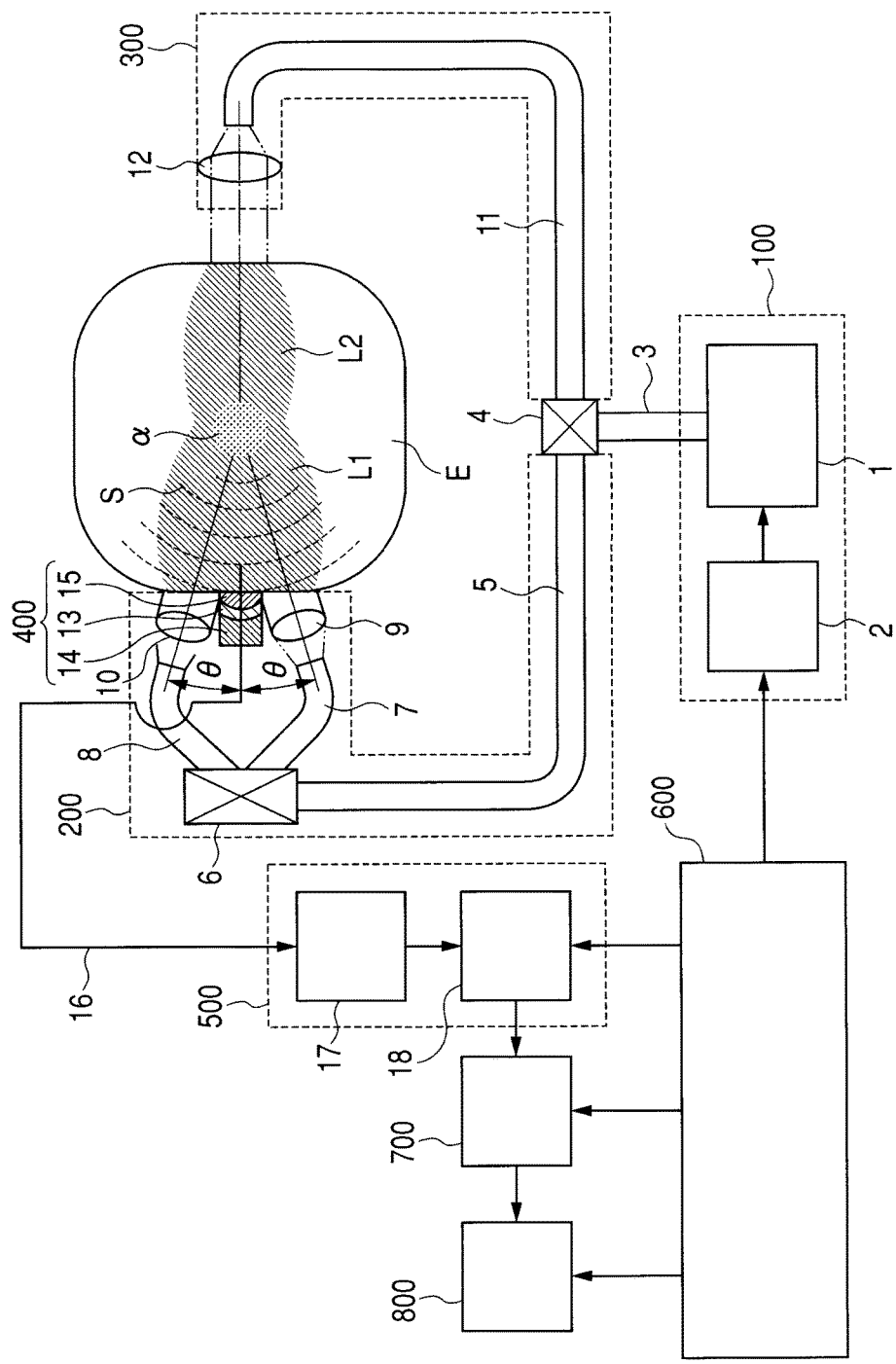
FIG. 1 is a diagram illustrating a schematic structure of a measurement apparatus according to Example 1 of the present invention.

Next, an embodiment of the present invention is described.

A measurement apparatus according to this embodiment of the present invention comprises: a light source unit for emitting a pulse beam; an illumination optical unit for leading the pulse beam emitted by the light source unit to an inside of an inspection object; and an acoustic signal detection unit for detecting a photoacoustic signal generated by the pulse beam led to the inside of the inspection object.

The illumination optical unit includes a first illumination optical unit and a second illumination optical unit that are arranged so that the inspection object is irradiated with the pulse beam from both sides thereof opposingly.

Further, the acoustic signal detection unit is disposed so that a detection surface of the acoustic signal detection unit is positioned on the same side as that of one of irradiation surfaces of the inspection object which the first illumination optical unit and the second illumination optical unit irradiate with the pulse beam.

Further, in the measurement apparatus according to the embodiment of the present invention, the one of the first illumination optical unit and the second illumination optical unit on the side on which the acoustic signal detection unit is disposed and the acoustic signal detection unit are disposed so that a center axis of axial symmetry of a region in which the first illumination optical unit illuminates the inspection object and a center axis of axial symmetry of a region in which the acoustic signal detection unit detects an acoustic signal coincide with each other.

Further, in the measurement apparatus according to the embodiment of the present invention, the first illumination optical unit and the second illumination optical unit are disposed so that a center axis of axial symmetry of a region in which the first illumination optical unit illuminates the inspection object and a center axis of axial symmetry of the region in which the second illumination optical unit illuminates the inspection object coincide with each other.

Further, the measurement apparatus according to the embodiment of the present invention may further comprise a scan drive unit for scan-driving the first illumination optical unit, the second illumination optical unit, and the acoustic signal detection unit with respect to the inspection object while maintaining a position relationship among the first illumination optical unit, the second illumination optical unit, and the acoustic signal detection unit.

Further, the measurement apparatus according to the embodiment of the present invention may further comprise a distance modifying unit for changing a distance between the first illumination optical unit and the second illumination optical unit.

Further, the measurement apparatus according to the embodiment of the present invention may further comprise, between the inspection object and the acoustic signal detection unit, a spacer formed of a member having a high transmittance property and a low attenuation property with respect to light from the light source unit and an acoustic wave.

Further, in the measurement apparatus according to the embodiment of the present invention, the illumination optical unit may be formed of an optical fiber.

Further, in the measurement apparatus according to the embodiment of the present invention, the illumination optical unit may be formed of an optical fiber and a lens.

Further, in the measurement apparatus according to the embodiment of the present invention, the illumination optical unit may be formed of an optical fiber, a lens, and an acousto-optic beam splitter.

Further, in the measurement apparatus according to the embodiment of the present invention, the illumination optical unit may be formed of a mirror, a beam splitter, and a lens.

The measurement apparatus according to the embodiment of the present invention may further comprise: a first plate and a second plate for holding the inspection object therebetween; and a plate drive mechanism for controlling pressure exerted on the inspection object by the first plate and the second plate.

EXAMPLES

Now, examples of the present invention are described.

Example 1

In Example 1, a structural example of a measurement apparatus to which the present invention is applied is described.

FIG. 1 is a diagram illustrating a schematic structure of the measurement apparatus according to this example.

The measurement apparatus of this example includes a pulse beam generator 100 (i.e., a light source unit), a first illumination optical system 200 (i.e., a first illumination optical unit), and a second illumination optical system 300 (i.e., a second illumination optical unit). In addition, the measurement apparatus includes an ultrasonic detector 400 (i.e., an acoustic signal detection unit), a signal analyzer 500, a controller 600, a memory 700, and a display 800.

An inspection object E is a biological tissue such as a breast, for example. An absorber $\alpha$ has an absorption larger than peripheral tissues and has a spherical shape, for example.

A schematic process for measuring the inspection object E by the measurement apparatus having the above-mentioned structure is described.

The pulse beam generator 100 emits light of a pulse beam of the nanosecond order, and the pulse beam is led by the first illumination optical system 200 and the second illumination optical system 300 to a surface of the inspection object E.

The pulse beam that has entered the inspection object E from the surface thereof propagates inside the tissue and reaches the absorber $\alpha$. Energy of the light that has reached the absorber $\alpha$ is absorbed and converted into thermal energy. Then, a transient rise of temperature occurs in the absorber $\alpha$, and the increased temperature is then relaxed.

On this occasion, the temperature rise and its relaxation causes an expansion and a contraction in the tissue including the absorber $\alpha$, which generates an elastic wave to be a photoacoustic signal S. The photoacoustic signal S generated from the absorber $\alpha$ propagates inside the tissue of the inspection object E and is detected by the ultrasonic detector 400.

In the present invention, the photoacoustic signal means an elastic wave (photoacoustic wave) itself generated by irradiating the inspection object with light, and the ultrasonic detector as the acoustic signal detection unit detects the photoacoustic signal as the photoacoustic wave.

Figure 2:
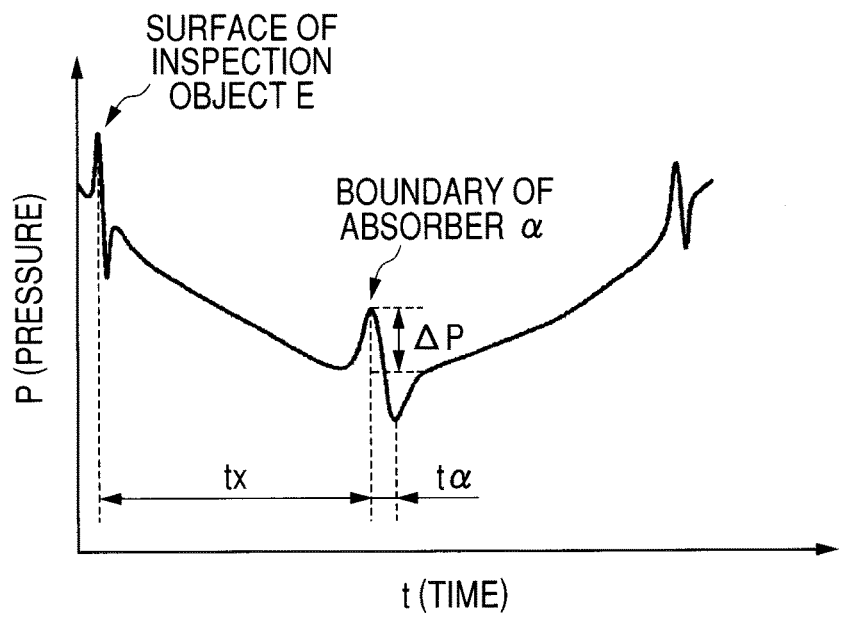
FIG. 2 is a graph illustrating a profile of a photoacoustic signal S generated from an inspection object E according to Example 1 of the present invention.

FIG. 2 illustrates a profile of the photoacoustic signal S generated from the inspection object E.

A propagation time tx of the photoacoustic signal S that is an elastic wave can be determined from a peak interval of a waveform generated from the surface of the inspection object E contacting with the ultrasonic detector 400 and from a boundary of the absorber $\alpha$.

In addition, a propagation time t$\alpha$ of the photoacoustic signal S propagating in the absorber $\alpha$ can be determined from a peak interval generated from the boundary of the absorber $\alpha$. When a sonic speed in the biological tissue is denoted by vs, the distance between the surface of the inspection object E and the absorber $\alpha$ as well as the size of the absorber $\alpha$ can be calculated. In other words, spatial position information of the absorber $\alpha$ in the inspection object E can be obtained.

In addition, an amplitude $\Delta P$ of a spike waveform generated from the absorber $\alpha$ indicates an intensity P$\alpha$ of the elastic wave generated in the absorber $\alpha$.

When an absorption coefficient of the absorber $\alpha$ is denoted by $\mu a$, energy fluence of light entering the absorber $\alpha$ is denoted by I$\alpha$, and Gruneisen parameter determined according to the biological tissue is denoted by $\Gamma$, the intensity P$\alpha$ of the elastic wave due to a photoacoustic effect generated in the absorber $\alpha$ can be calculated by the following equation.

$P\alpha\alpha = \frac{1}{2}\mu a \cdot \Gamma \cdot I\alpha$

The energy fluence of light propagating in an absorption dispersion medium such as a biological tissue can be calculated by using a light diffusion equation and a transport equation, and thus Iα can be calculated.

The amplitude ΔP measured by the ultrasonic detector 400 includes an influence of attenuation of the elastic wave generated in the absorber α when the elastic wave propagates in the biological tissue. Therefore, the intensity Pα can be calculated by subtracting the influence of attenuation.

As described above, the absorption coefficient μa of the absorber α in the inspection object E can be calculated.

The signal analyzer 500 calculates the position of the absorber α based on time characteristics of the detected photoacoustic signal and calculates the absorption coefficient μa based on intensity characteristics.

Further, the signal analyzer 500 reconstructs a spatial distribution of the absorption coefficient μa in the absorber α and its periphery, whereby an image of the absorption characteristics in the inspection object E is generated.

The controller 600 stores the calculated position of the absorber α and the calculated absorption coefficient μa in the memory 700 and displays a spatial distribution image of the absorption coefficient μa on the display 800.

Hereinafter, details of individual components are described.

The pulse beam generator 100 is a light source unit that emits a pulse beam of the nanosecond order with a specific wavelength for irradiating the inspection object E, and the pulse beam generator 100 includes a laser light source 1 and a laser driver 2.

The wavelength of light emitted from the laser light source 1 is selected to be a wavelength corresponding to absorption spectrums of water, fat, protein, oxyhemoglobin, reduced hemoglobin, and the like constituting the biological tissue.

As an example, a wavelength within a range from 600 to 1,500 nm is appropriate because the light of this wavelength is hardly absorbed by water that is a main ingredient of the tissue inside the biological tissue so that the light can permeate well, and it has characteristic spectrums of fat, oxyhemoglobin, and reduced hemoglobin.

In addition, it is known that new blood vessels are formed and consumption of oxygen is increased when a tumor such as a cancer grows in a biological tissue.

Figure 3:
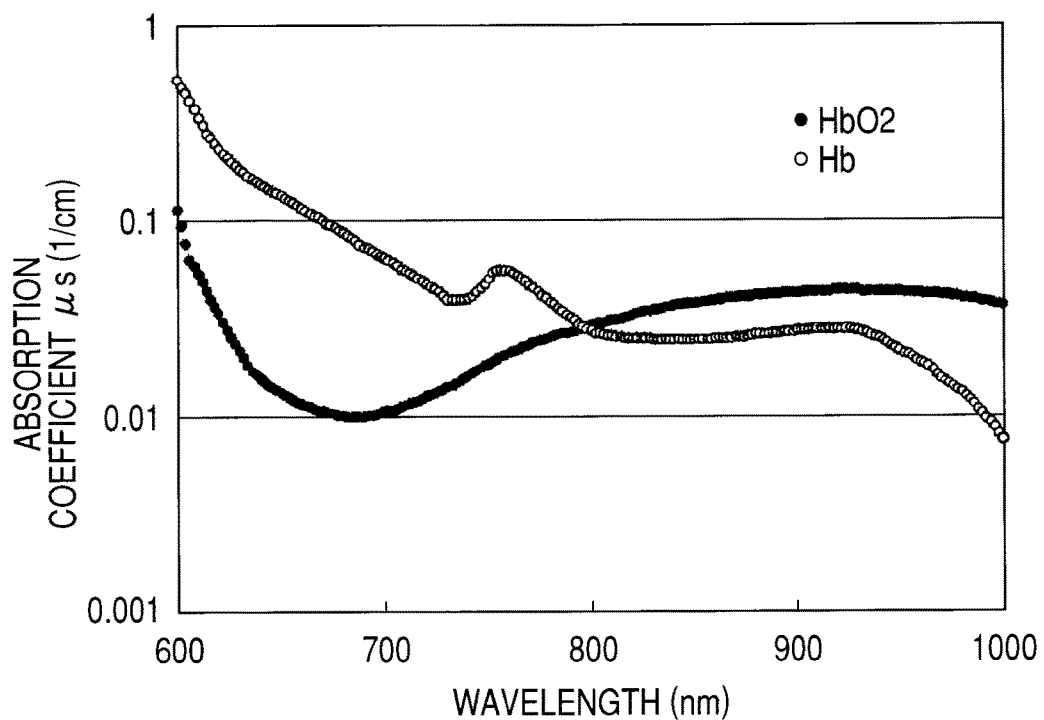
FIG. 3 is a graph illustrating absorption spectrums of $HbO_2$ and Hb in a range of wavelength from 600 to 1,000 nm according to Example 1 of the present invention.

As a method involving evaluating a formation of new blood vessels and an increase in consumption of oxygen, it is possible to utilize characteristics of the absorption spectrums of the oxyhemoglobin ($HbO_2$) and the reduced hemoglobin (Hb). FIG. 3 illustrates absorption spectrums of $HbO_2$ and Hb in the range of wavelength from 600 to 1,000 nm.

The measurement apparatus measures concentration values of Hb and $HbO_2$ contained in blood in a biological tissue based on the absorption spectrums of $HbO_2$ and Hb with respect to multiple wavelengths.

Then, the concentrations of Hb and $HbO_2$ are measured at multiple positions, and an image of concentration distribution is created so that a region in which new blood vessels are formed in the biological tissue can be distinguished.

In addition, an oxygen saturation is calculated based on the concentrations of Hb and $HbO_2$ so that a region in which consumption of oxygen is increased can be distinguished based on the oxygen saturation.

In this way, the spectral information of Hb and $HbO_2$ measured by the measurement apparatus can be utilized for diagnostics.

In this example, as wavelengths near 800 nm at which the absorption characteristics of Hb and $HbO_2$ cross each other as illustrated in FIG. 3, two wavelengths λ1=700 nm and λ2=850 nm are used.

As an example of a specific light source, it may be formed of a semiconductor laser generating different wavelengths, a variable wavelength laser, or the like.

The first illumination optical system 200 and the second illumination optical system 300 are illumination optical units for leading the pulse beam emitted from the pulse beam generator 100 to the inspection object E.

The pulse beam emitted from the laser light source 1 is led by an optical fiber 3 to a first beam splitter 4. The pulse beam entering the first beam splitter 4 is divided into two beams, which are led respectively to the first illumination optical system 200 and the second illumination optical system 300.

The first illumination optical system 200 includes an optical fiber 5, a second beam splitter 6, optical fibers 7 and 8, and lenses 9 and 10.

The pulse beam that has entered the optical fiber 5 is divided into two beams by the second beam splitter 6, and the beams are respectively led to the optical fibers 7 and 8.

The pulse beam that has entered the optical fiber 7 is enlarged by the lens 9 that is obliquely disposed by an angle θ with respect to the ultrasonic detector 400, whereby the surface of the inspection object E is illuminated from one side of the ultrasonic detector 400. Similarly, the pulse beam that has entered the optical fiber 8 is enlarged by the lens 10 that is obliquely disposed by an angle θ with respect to the ultrasonic detector 400 in a direction opposite to the lens 9, whereby the surface of the inspection object E is illuminated from the other side of the ultrasonic detector 400.

The second illumination optical system 300 is disposed so as to be opposed to the first illumination optical system 200 via the inspection object disposed therebetween, and center axes of axial symmetry of the regions illuminated by the first illumination optical system 200 and the second illumination optical system 300 coincide with each other. In other words, the inspection object is irradiated with the pulse beams on both sides thereof because the first illumination optical system and the second illumination optical system are opposed to each other via the inspection object disposed therebetween.

According to this structure, energies of lights that are projected from the illumination optical systems simultaneously are combined in the inspection object E, and hence the energy fluence of light that reaches a deep part of the inspection object can be increased.

The second illumination optical system 300 includes an optical fiber 11 and a lens 12. The pulse beam that has entered the optical fiber 11 is enlarged by the lens 12 and is led to the surface of the inspection object E.

In this example, one light source and the beam splitters are used for leading the pulse beam to the first and second illumination optical systems. However, it is possible to dispose light sources respectively to the individual illumination optical systems.

In this case, it is preferable to drive the two light sources simultaneously in a synchronized manner so that energy fluences of light can be combined.

On this occasion, it is preferable to drive the two light sources in a completely simultaneous manner, but the effect of combining the energy fluences of light can be obtained if the two light sources are driven within a pulse width of the pulse beam or a thermal relaxation time of the inspection object E.

Therefore, the expression of "to drive the two light sources simultaneously" in the present invention is used to mean "to drive the two light sources within the thermal relaxation time of the inspection object E or within the pulse width of the pulse beam".

In addition, it is preferable that center axes of axial symmetry of the regions illuminated by the illumination optical systems coincide with each other, but the effect of combining the energy fluences of light can be obtained if full widths at half maximum of individual illumination light intensity distributions overlap each other partially.

Therefore, the expression of "coincide with each other" concerning the center axes of axial symmetry in the present invention is used to mean "full widths at half maximum of individual illumination light intensity distributions overlap each other partially" concerning the two illuminated regions of axial symmetry.

The ultrasonic detector 400 is an acoustic signal detection unit for detecting a photoacoustic signal S (photoacoustic wave) generated in the inspection object E, and is disposed on the same side as that of an irradiation surface of the first illumination optical system 200. In other words, the ultrasonic detector is disposed so that a detection surface of the ultrasonic detector 400 is positioned on the same side as that of the irradiation surface for the first illumination optical system 200 to irradiate the inspection object with the pulse beam, with respect to the inspection object.

Here, the detection surface of the ultrasonic detector is a surface for receiving the photoacoustic wave with an ultrasonic oscillator 13 of the ultrasonic detector 400. In addition, the irradiation surface is the surface on the inspection object that is irradiated with the pulse beam from the first illumination optical system 200 in this example. The side on which the second illumination optical system 300 is disposed is opposite to the side on which the ultrasonic detector and the first illumination optical system are disposed, via the inspection object disposed therebetween.

Further, in other words about the position of the ultrasonic detector, the ultrasonic detector 400 is disposed so as to be opposed to the surface facing the inspection object in the first illumination optical system 200 (the surface may also be the surface contacting with the inspection object). Here, the expression "to be opposed" also includes the case where the surface of the ultrasonic detector 400 that is closest to the inspection object (i.e., the detection surface) is the same as the surface of the first illumination optical system 200 that faces the inspection object.

The ultrasonic detector 400 has a circular shape, and FIG. 1 illustrates its cross section including the center axis of the circle.

The ultrasonic oscillator 13 having a concave shape is disposed on a backing member 14, and an acoustic matching layer 15 is provided to the ultrasonic oscillator 13 on the side close to the inspection object E.

A lead wire 16 is connected to the ultrasonic oscillator 13.

The ultrasonic oscillator 13 includes a piezoelectric element having a piezoelectric effect for converting a change in pressure due to the received photoacoustic signal S into voltage (electric signal).

As the piezoelectric element, a piezoelectric ceramic material such as lead zirconate titanate (PZT) or a polymer piezoelectric film material such as polyvinylidene difluoride (PVDF) can be used.

In addition, the center of the concave surface of the ultrasonic oscillator 13 is set to the position of the absorber α, whereby the photoacoustic signal S generated from the vicinity of the absorber α can be selectively received.

The backing member 14 is used for suppressing unnecessary oscillation of the ultrasonic oscillator 13. An example of a material that constitutes the backing member 14 includes polyurethane resin or silicone rubber. The acoustic matching layer 15 is disposed for transmitting the photoacoustic signal S effectively.

In general, the piezoelectric element material and the biological tissue have acoustic impedance values that are largely different from each other. Therefore, if the piezoelectric element material contacts directly with the biological tissue, the photoacoustic signal cannot be transmitted effectively because of a large reflection on an interface therebetween.

Therefore, the acoustic matching layer 15 made of a material having intermediate acoustic impedance is disposed between the piezoelectric element material and the biological tissue, whereby the reflection on the interface is decreased to transmit the photoacoustic signal S effectively.

As an example of the material constituting the acoustic matching layer 15, there is epoxy resin, silica glass, or the like.

The lead wire 16 transmits the electric signal generated by the conversion of the photoacoustic signal S in the ultrasonic oscillator 13 to the signal analyzer 500.

Further, the ultrasonic oscillator 13 may be formed of not only the piezoelectric element but also an element for detecting a change in capacitance.

The concave ultrasonic oscillator is used in this example, but it is possible to use a flat ultrasonic oscillator and an acoustic lens. In addition, it is possible to use an ultrasonic probe having multiple ultrasonic oscillators arranged in an array, which is used in an ultrasonic echo apparatus or in non-destructive inspection.

As described above, the first illumination optical system 200 and the second illumination optical system 300 are disposed so as to be opposed to each other, center axes of axial symmetry of the regions illuminated by these illumination optical systems coincide with each other, and the ultrasonic detector 400 is disposed on the same side as that of the first illumination optical system 200.

According to this structure, the photoacoustic signal S can be detected with higher contrast compared with the conventional example described above.

In addition, the center axis of axial symmetry of the first illumination optical system 200 is made to coincide with the center axis of the ultrasonic detector 400 in the structure of FIG. 1.

Figure 4:
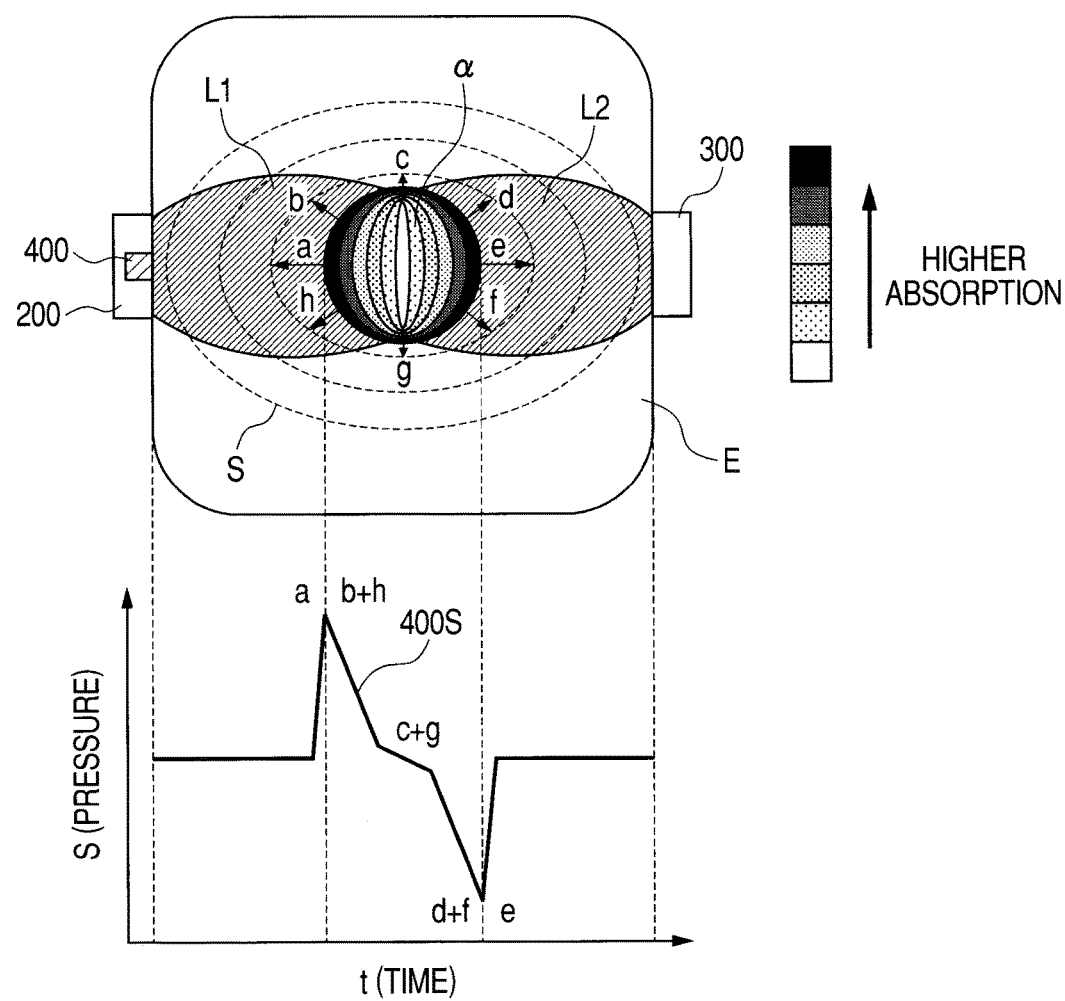
FIG. 4 is a diagram illustrating the photoacoustic signal S in a spherical absorber received by an ultrasonic detector according to Example 1 of the present invention.

FIG. 4 is a diagram illustrating the photoacoustic signal S in the spherical absorber α received by the ultrasonic detector 400.

The pulse beam that irradiates the inspection object E propagates into a deep part thereof while being attenuated by influences of absorption and dispersion in the biological tissue.

In FIG. 4, L1 indicates the energy fluence of light that has been projected from the first illumination optical system 200 and has propagated in the inspection object E, and L2 indicates that of light projected from the second illumination optical system 300.

Forward dispersion is generally strong among dispersions in a biological tissue, and hence the energy of the projected light is dispersed and propagates mainly in a light incidence axis direction.

Therefore, as to the absorption of light energy in the absorber α in the inspection object E, the absorption increases on the side of light incidence. The absorption of light energy becomes maximum at positions 'a' and 'e' in the illustrated absorber α, while becomes smaller at positions 'c' and 'g'.

In addition, the absorption of light energy becomes large in the vicinity of the surface of the absorber α, and hence the energy of light that reaches a deep part of the absorber to be absorbed becomes small.

Pressure intensity of the photoacoustic signal generated from the absorber α having such a light energy absorption distribution becomes high when the absorption of light energy is large and becomes low when the absorption of light energy is small.

When the photoacoustic signal S generated from the absorber α is received by the ultrasonic detector 400, a signal with high pressure generated from a vicinity of positions 'a', 'b' and 'h' that are close to the ultrasonic detector 400 is first detected.

Next, a signal with low pressure generated from a vicinity of the positions 'c' and 'g' having the same distance from the ultrasonic detector 400 is detected. Finally, a signal with high pressure generated from a vicinity of positions 'd', 'e' and 'f' is detected. Here, 400S denotes a profile of the photoacoustic signal S generated from the absorber α, which is received by the ultrasonic detector 400.

The first peak of the photoacoustic signal S is generated in a photoacoustic compression phase. In contrast, the second peak is generated in a expansion phase, corresponding to a reflected wave in which the phase of the wave generated in the compression phase is inverted by a difference in acoustic impedance between the absorber α and a tissue of its periphery.

Figure 5:
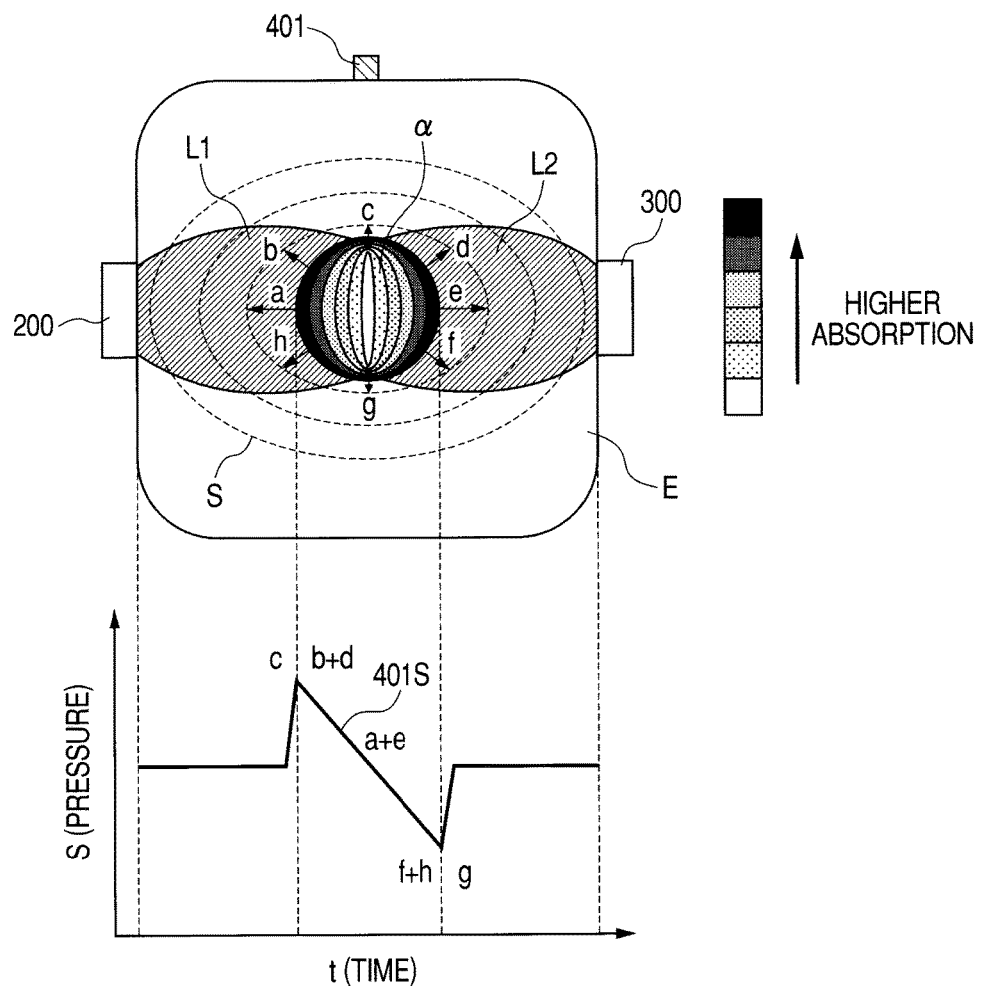
FIG. 5 is a diagram illustrating a structure of a conventional example (similar to that of US 2004/0127783) in which a ultrasonic detector is disposed on a surface perpendicular to a first illumination optical system as an example of disposing the ultrasonic detector on a surface different from the first illumination optical system.

FIG. 5 illustrates a structure of a conventional example (similar to that of US 2004/0127783) in which an ultrasonic detector 401 is disposed on a surface perpendicular to the first illumination optical system 200 as an example of disposing the ultrasonic detector 401 on a surface different from the first illumination optical system 200.

A light energy absorption distribution similar to that described above with reference to FIG. 4 is generated in the absorber α.

When the photoacoustic signal S generated from the absorber α is received by the ultrasonic detector 401, a signal with low pressure generated from a vicinity of positions 'b', 'c' and 'd' that are close to the ultrasonic detector 401 is first detected.

Next, a signal with high pressure generated from a vicinity of positions 'a' and 'e' having the same distance from the ultrasonic detector 401 is detected. Finally, a signal with low pressure generated from a vicinity of positions 'f', 'g' and 'h' is detected.

Here, 401S denotes a profile of the photoacoustic signal S generated from the absorber α, which is received by the ultrasonic detector 401.

Figure 6:
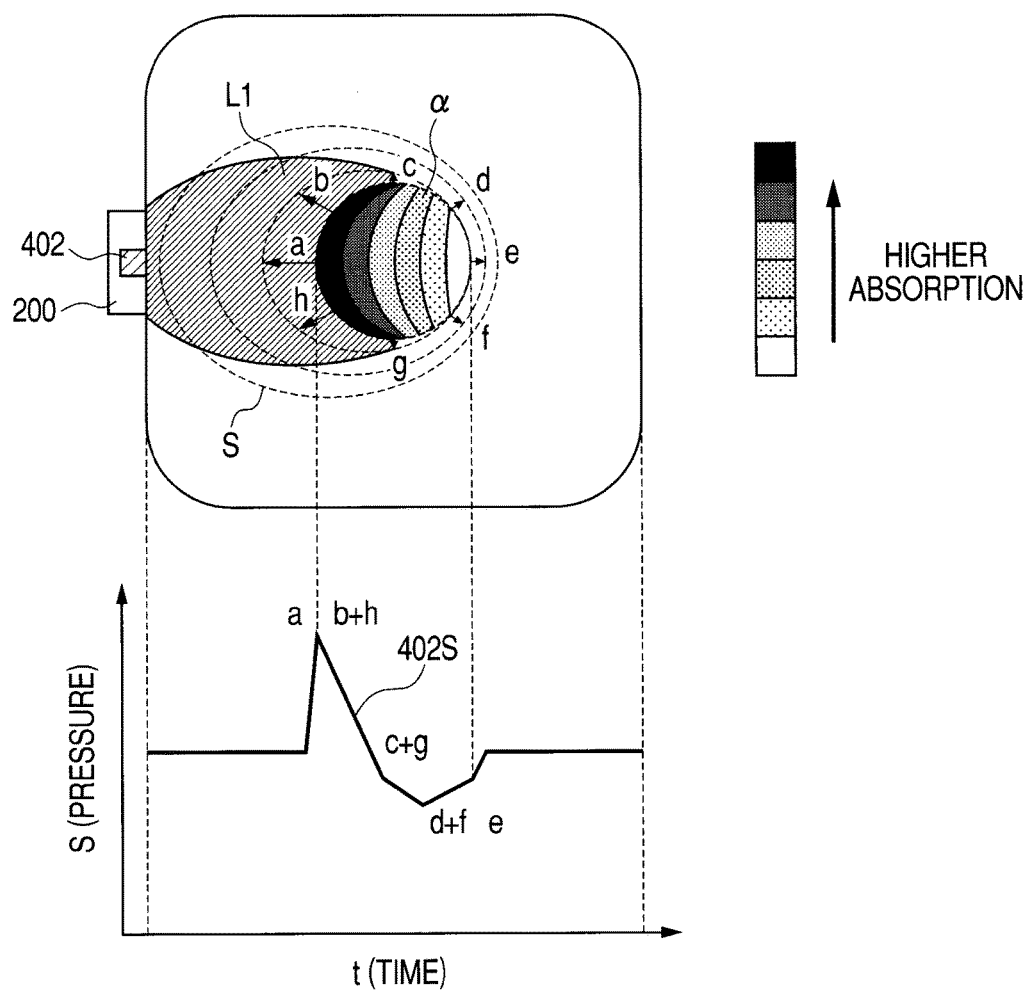
FIG. 6 is a diagram illustrating a structure of a conventional example (similar to that of Japanese Patent Application Laid-Open No. 2005-021380) in which a second illumination optical system is eliminated from the structure of FIG. 4.

FIG. 6 illustrates a structure of a conventional example (similar to that of Japanese Patent Application Laid-Open No. 2005-021380) in which the second illumination optical system 300 is eliminated from the structure of FIG. 4.

The absorption of light energy is largest at the position 'a' on the light incidence side in the illustrated absorber α, and is second largest at the positions 'b' and 'h'. Further, the absorbed energy of light becomes smaller in the order of the positions 'c' and 'g', the positions 'd' and 'f', and the position 'e' as going to a deeper part of the absorber.

When the photoacoustic signal S generated from the absorber α is received by an ultrasonic detector 402, a signal with high pressure generated from a vicinity of the positions 'a', 'b' and 'h that are close to the ultrasonic detector 402 is first detected.

Next, a signal with low pressure generated from a vicinity of the positions 'c' and 'g' having the same distance from the ultrasonic detector 402 is detected. Finally, a signal with low pressure generated from a vicinity of the positions 'd', 'e' and 'f' is detected.

Here, 402S denotes a profile of the photoacoustic signal S generated from the absorber α, which is received by the ultrasonic detector 402.

Figure 7:
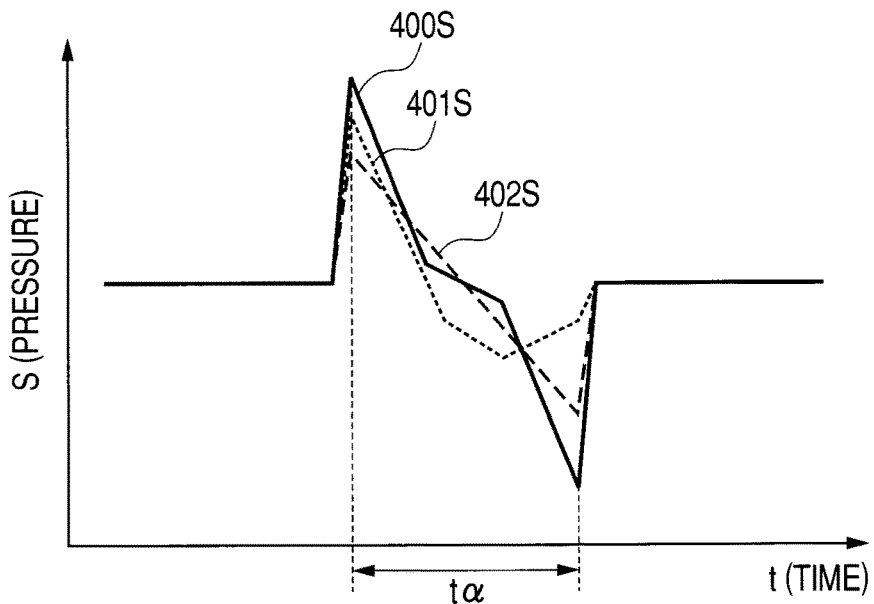
FIG. 7 is a graph comparing a detection signal profile of the ultrasonic detector illustrated in FIG. 4 according to Example 1 of the present invention with detection signal profiles of the ultrasonic detectors illustrated in FIGS. 5 and 6 according to the conventional examples.

FIG. 7 illustrates a graph comparing the detection signal profile 400S of the ultrasonic detector 400 of this example illustrated in FIG. 4 with the detection signal profile 401S of the ultrasonic detector 401 of the conventional example illustrated in FIG. 5 as well as the detection signal profile 402S of the ultrasonic detector 402 of the conventional example illustrated in FIG. 6.

As illustrated in FIG. 7, a pressure of the photoacoustic signal S generated from a vicinity of the boundary of the absorber α is largest in the detection signal profile 400S.

The position and the size of the absorber α are calculated by using a time read from the peak in the photoacoustic signal generated from the boundary of the absorber α.

In the present invention the time can be read by using a higher contrast signal, and hence the position and the size of the absorber α can be calculated more accurately than the conventional example.

The signal analyzer 500 includes a calculation processing portion 17 and an image generating portion 18.

The calculation processing portion 17 calculates the position of the absorber α based on time characteristics of the detected photoacoustic signal S and calculates the absorption coefficient $\mu a$ based on the intensity characteristics.

The image generating portion 18 generates a distribution image of the absorption coefficient $\mu a$ in the inspection object E on the basis of the calculated spatial position and the absorption coefficient $\mu a$ of the absorber α in the inspection object E.

The controller 600 is connected to the laser driver 2 of the pulse beam generator 100 and controls the timing, the light intensity, and the like of emission of the pulse beam.

In addition, the controller 600 is connected to the signal analyzer 500, the memory 700 and the display 800 as well.

The controller 600 stores the spatial position and the absorption coefficient $\mu a$ of the absorber α in the inspection object E which are calculated by the signal analyzer 500 as well as the distribution image of the absorption coefficient $\mu a$ in the memory 700, and controls the display 800 to display the distribution image of the absorption coefficient $\mu a$ in the inspection object E.

As the memory 700, it is possible to use a data recording device such as an optical disk, a magnetic disk, a semiconductor memory or a hard disk.

As the display 800, it is possible to use a display device such as a liquid crystal display, a CRT or an organic EL display.

Next, the step of obtaining a spectral characteristic image of the inside of the tissue of the inspection object E with the measurement apparatus according to this example is described.

In the first step, the first illumination optical system 200, the second illumination optical system 300 and the ultrasonic detector 400 are made to contact with the surface of the inspection object E. When a measurement start switch (not shown) is activated, the pulse beam generator 100 is driven to emit light of a pulse beam of the nanosecond order having a wavelength λ1=700 nm.

Next, in the second step, the first illumination optical system 200 and the second illumination optical system 300 irradiate the inspection object E with the pulse beam.

Next, in the third step, the photoacoustic signal S generated in the inspection object E is detected by the ultrasonic detector 400.

Next, in the fourth step, the signal analyzer 500 calculates the position and the size of the absorber α based on time characteristics of the detected photoacoustic signal S, calculates the absorption coefficient μa based on the intensity characteristics, and generates an image in which the spatial distribution of the absorption coefficient μa at the absorber α and its periphery is reconstructed.

Next, in the fifth step, the controller 600 stores the calculated position information of the absorption coefficient μa of the wavelength λ1 and the image in the memory 700.

Next, in the sixth step, the controller 600 sets the wavelength λ2 of emission light of the pulse beam generator 100 to be 850 nm. The pulse beam generator 100 is driven so that the pulse beam of light of the nanosecond order having the wavelength λ2=850 nm is emitted.

In the seventh step after conducting steps that are similar to the second step, the third step and the fourth step, the controller 600 stores the calculated position information of the absorption coefficient μa at the wavelength λ2 and the image in the memory 700.

Next, in the eighth step, the controller 600 superimposes the distribution images of the absorption coefficient μa at the wavelengths λ1 and λ2, which are displayed on the display 800.

Finally, in the ninth step, the measurement is finished.

FIGS. 8 to 13 are diagrams illustrating other structural examples concerning the first illumination optical system and the ultrasonic detector.

A member denoted by the same reference symbol as in FIG. 1 has the same function as described above with reference to FIG. 1.

Figure 8:
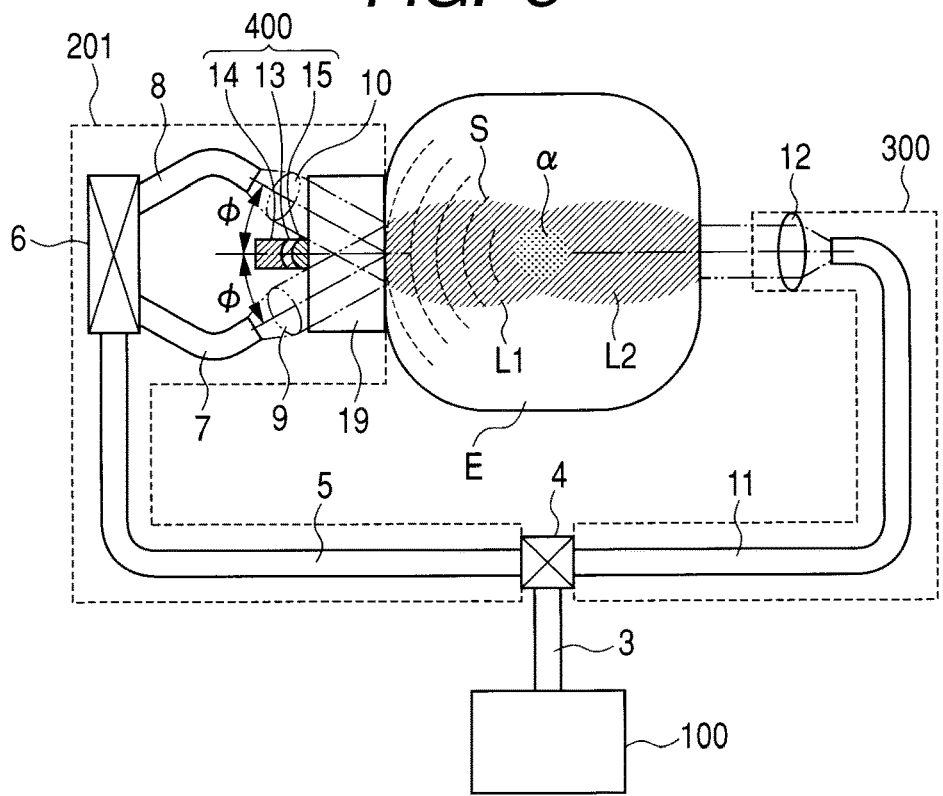
FIG. 8 is a diagram illustrating another structural example of the first illumination optical system and the ultrasonic detector according to Example 1 of the present invention.

A first illumination optical system 201 illustrated in FIG. 8 corresponds to the first illumination optical system 200 illustrated in FIG. 1 except that the angle θ is replaced with φ, and a spacer 19 is disposed between the inspection object and the ultrasonic detector (acoustic signal detection unit).

The spacer 19 is formed of a member having a high transmittance property and a low attenuation property with respect to light and an acoustic wave emitted from the pulse beam generator 100.

An example of a material constituting the spacer 19 includes polymethyl pentene polymer, polycarbonate, acrylic resin and the like. Light beams going out from the lenses 9 and 10 with the angle φ can be superimposed on the surface of the inspection object E via the spacer 19.

In addition, according to the structure illustrated in FIG. 8, similarly to the case illustrated in FIG. 1, the center axis of axial symmetry of the first illumination optical system 201 can be made to coincide with the center axis of the ultrasonic detector 400.

Figure 9:
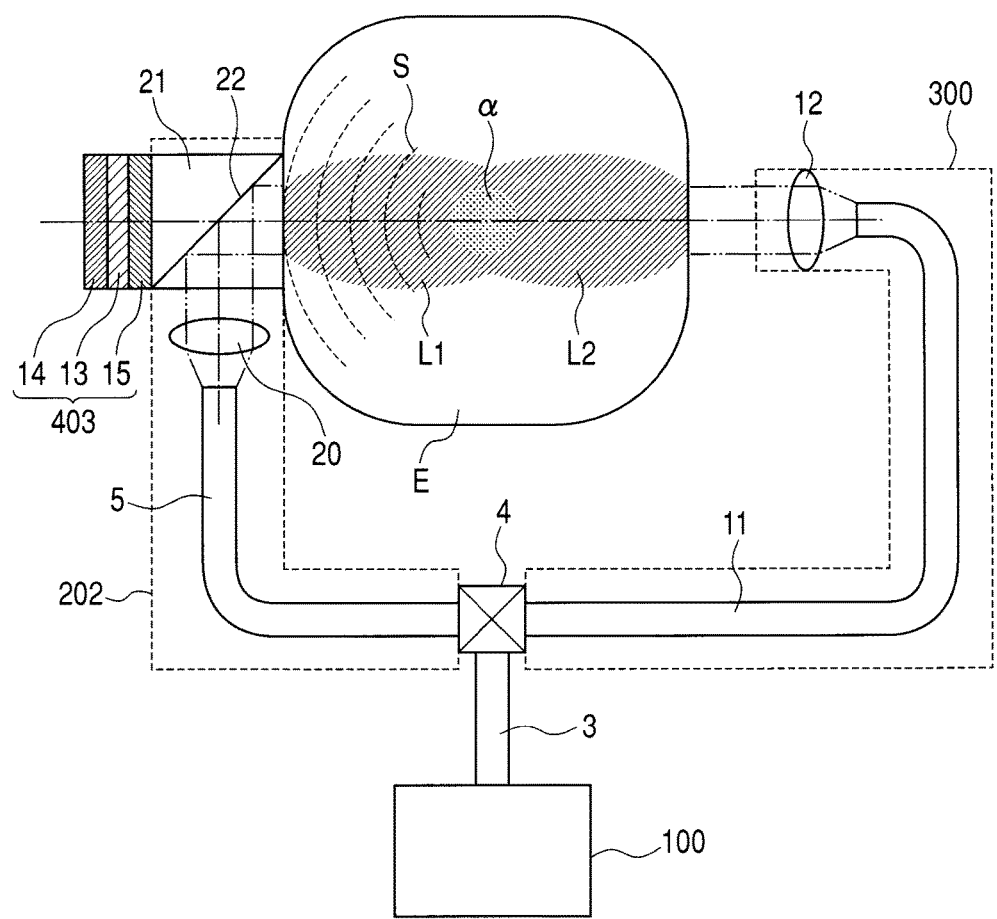
FIG. 9 is a diagram illustrating another structural example of the first illumination optical system and the ultrasonic detector according to Example 1 of the present invention.

A first illumination optical system 202 illustrated in FIG. 9 includes the optical fiber 5, a lens 20, and an acousto-optic beam splitter 21.

The acousto-optic beam splitter 21 reflects light emitted from the pulse beam generator 100 and permits the acoustic wave such as the photoacoustic signal S to pass therethrough.

The acousto-optic beam splitter 21 includes the above-mentioned material having a high transmittance property and a low attenuation property with respect to the light for irradiation and the acoustic wave, and a thin film layer 22 such as aluminum or silver having high reflection characteristics with respect to the light for irradiation, which is formed on the material.

There is a large difference in acoustic impedance between the above-mentioned resin material and the metal material used for the thin film layer, but the thin film layer made of the metal material has little influence because its thickness of approximately a few microns is sufficiently small compared with the wavelength of the acoustic wave.

An ultrasonic detector 403 is a 2D array probe having a circular shape and is disposed so that its detection surface contacts with the acousto-optic beam splitter 21.

FIG. 9 is a cross section cut by a plane including the center axis of the circle. Multiple ultrasonic oscillators 13 having a small prism shape are arranged on the backing member 14.

The acoustic matching layer 15 is disposed on the side of the ultrasonic oscillator 13 that is closer to the inspection object E.

The ultrasonic detector 400 illustrated in FIG. 1 uses the circular concave ultrasonic oscillator, but the ultrasonic detector 403 obtains a desired position signal by using the Sum And Delay Beam forming method based on the photoacoustic signal received by the multiple ultrasonic oscillators 13.

The pulse beam emitted from the pulse beam generator 100 passes through the optical fiber 5 and is enlarged by the lens 20, and afterward the pulse beam is led to the acousto-optic beam splitter 21 and is reflected by the thin film layer 22 so as to be led to the surface of the inspection object E.

The photoacoustic signal S generated by the absorber α of the inspection object E propagates inside the inspection object E and the acousto-optic beam splitter 21 and is detected by the ultrasonic detector 403.

In this way, according to the structure illustrated in FIG. 9, the center axis of the first illumination optical system 202 and the center axis of the ultrasonic detector 403 can be made to coincide with each other by using the acousto-optic beam splitter 21.

Figure 10:
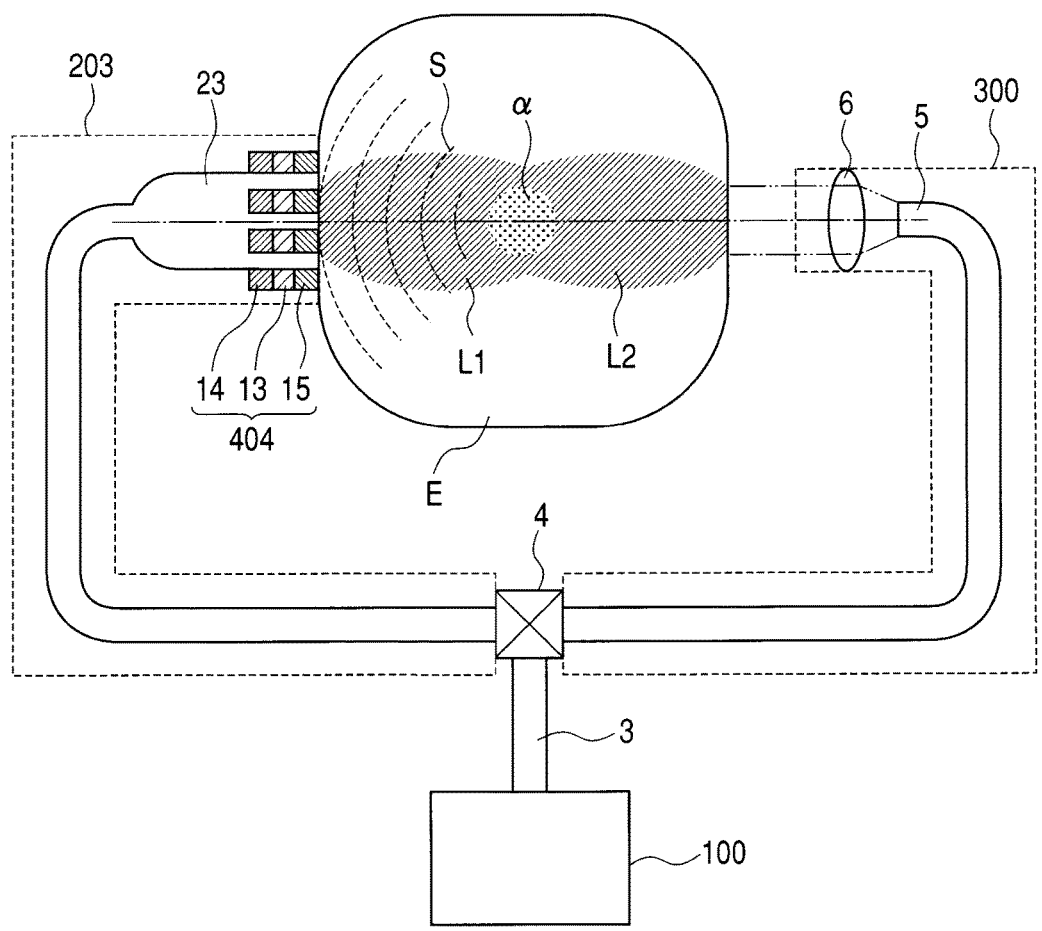
FIG. 10 is a diagram illustrating another structural example of the first illumination optical system and the ultrasonic detector according to Example 1 of the present invention.

A first illumination optical system 203 illustrated in FIG. 10 includes an optical fiber 23.

On one end of the optical fiber 23 that is closer to the inspection object E, the optical fiber is divided into multiple fibers.

An ultrasonic detector 404 is a 2D array probe that is similar to the one described above with reference to FIG. 9. There are gaps among the multiple arranged ultrasonic oscillators 13, and the divided portions of the optical fiber 23 are disposed in the gaps.

The pulse beam emitted from the pulse beam generator 100 passes through the optical fiber 23 and is led to the surface of the inspection object E. The photoacoustic signal S generated by the absorber α of the inspection object E propagates inside the inspection object E and is detected by the ultrasonic detector 404.

In this way, according to the structure illustrated in FIG. 10, the center axis of the first illumination optical system 203 and the center axis of the ultrasonic detector 404 can be made to coincide with each other by leading light from the gaps among array probes to the inspection object E.

Figure 11:
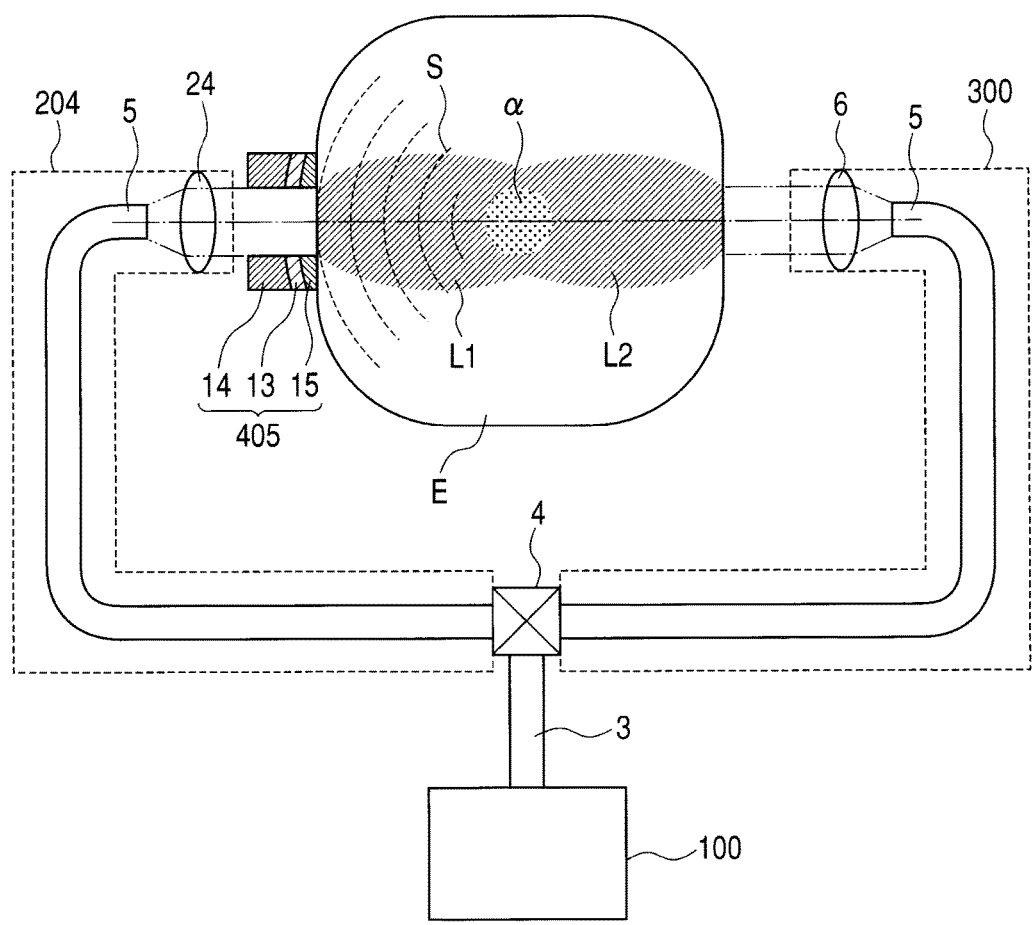
FIG. 11 is a diagram illustrating another structural example of the first illumination optical system and the ultrasonic detector according to Example 1 of the present invention.

A first illumination optical system 204 illustrated in FIG. 11 includes the optical fiber 5 and a lens 24. An ultrasonic detector 405 has an annular shape with a circular opening part at the center portion thereof, and FIG. 11 is a cross section cut by a plane including the center axis of the circle.

The ultrasonic oscillator 13 has a concave surface, and the center of the concave surface is set to a position of the absorber α.

Thus, the photoacoustic signal S generated from a vicinity of the absorber α can be selectively received.

The pulse beam emitted from the pulse beam generator 100 passes through the optical fiber 5 and is enlarged by the lens 24, and afterward the pulse beam is led to the surface of the inspection object E through the circular opening part of the ultrasonic detector 405.

The photoacoustic signal S generated by the absorber α of the inspection object E propagates inside the inspection object E and is detected by the ultrasonic detector 405.

In this way, according to the structure illustrated in FIG. 11, the center axis of the first illumination optical system 204 and the center axis of the ultrasonic detector 405 can be made to coincide with each other by leading light to the inspection object E through the circular opening part of the ultrasonic detector 405.

Figure 12:
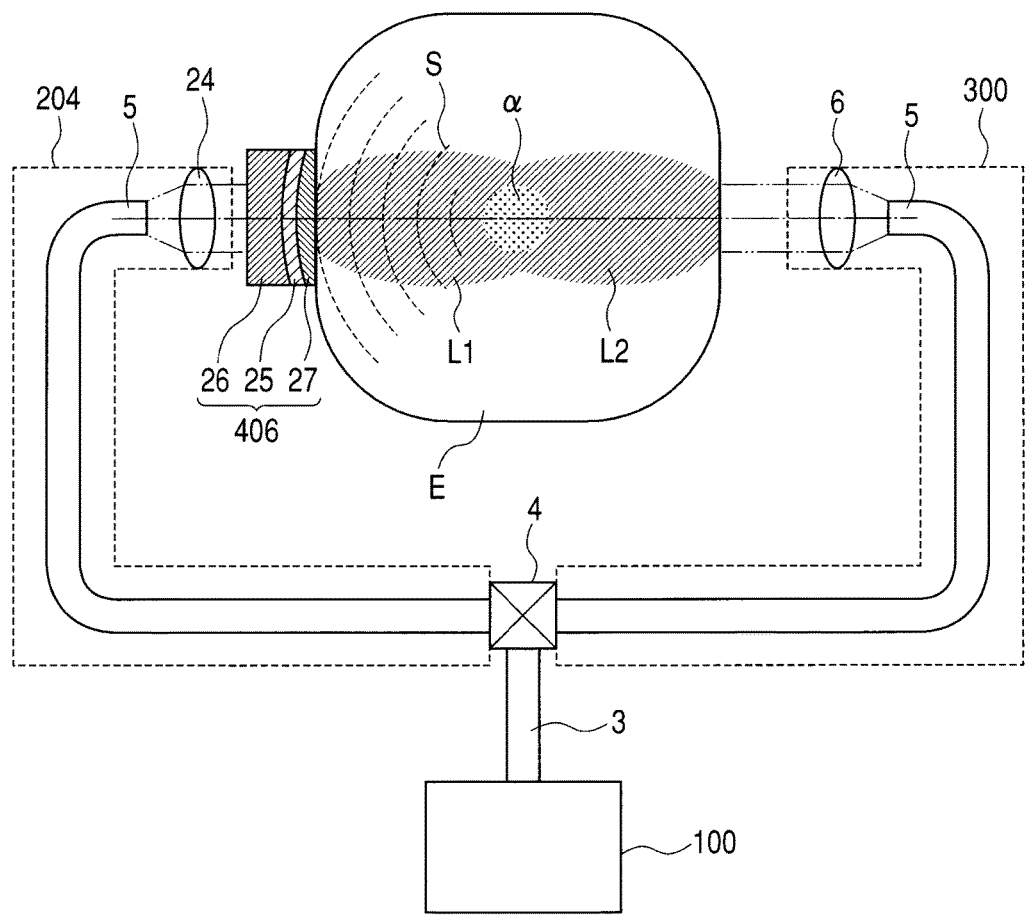
FIG. 12 is a diagram illustrating another structural example of the first illumination optical system and the ultrasonic detector according to Example 1 of the present invention.

The first illumination optical system 204 illustrated in FIG. 12 is the same as one described above with reference to FIG. 11.

An ultrasonic detector 406 includes an ultrasonic oscillator 25, a backing member 26, and an acoustic matching layer 27.

Those structural members have a high transmittance property and a low attenuation property with respect to light emitted from the pulse beam generator 100.

As an example of a material constituting the ultrasonic oscillator 25, lead zinc niobate titanate (PZNT) or the like can be used.

As an example of a material constituting the backing member 26 and the acoustic matching layer 27, a material similar to the one described above with reference to FIG. 1 can be used.

In addition, the ultrasonic oscillator 25 has a concave surface, and the center of the concave surface is set to a position of the absorber α. Thus, the photoacoustic signal S generated from a vicinity of the absorber α can be selectively received.

The pulse beam emitted from the pulse beam generator 100 passes through the optical fiber 5 and is enlarged by the lens 24, and afterward the pulse beam passes through the ultrasonic detector 406 and is led to the surface of the inspection object E.

The photoacoustic signal S generated by the absorber α of the inspection object E propagates inside the inspection object E and is detected by the ultrasonic detector 406.

In this way, according to the structure illustrated in FIG. 12, the center axis of the first illumination optical system 204 and the center axis of the ultrasonic detector 406 can be made to coincide with each other by leading light to the inspection object E after passing through the ultrasonic detector 406.

In this way, according to the structures illustrated in FIGS. 1 and 8 to 12, the ultrasonic detector 400 is disposed on the side closer to the first illumination optical system 200. In this way, the inspection object is irradiated on both sides thereof with light from the multiple illumination optical systems, and the ultrasonic detector is disposed so that the irradiation surface of one of the illumination optical systems and the detection surface of the ultrasonic detector are positioned on the same side with respect to the inspection object. Further, the center axes of axial symmetry of the regions illuminated by the first illumination optical system and the second illumination optical system that are disposed on both sides of the inspection object so as to be opposed to each other coincide with each other, and further the center axis of the ultrasonic detector disposed on the same surface as that of the first illumination optical system is made to coincide with those center axes. Therefore, the signal can be detected with high contrast.

In addition, it is preferable that the center axes of axial symmetry of the illuminated regions and the center axis of the ultrasonic detector coincide with each other, but the effect of detecting the high contrast signal can be obtained if the full width at half maximum of the illumination light intensity distribution overlaps partially with the full width at half maximum of the ultrasonic detection region.

Therefore, the expression of "coincide with each other" concerning the center axes in the present invention is used to mean "the full width at half maximum of the illumination light intensity distribution of axial symmetry of the illuminated regions overlaps partially with the full width at half maximum of the ultrasonic detection region".

Figure 13:
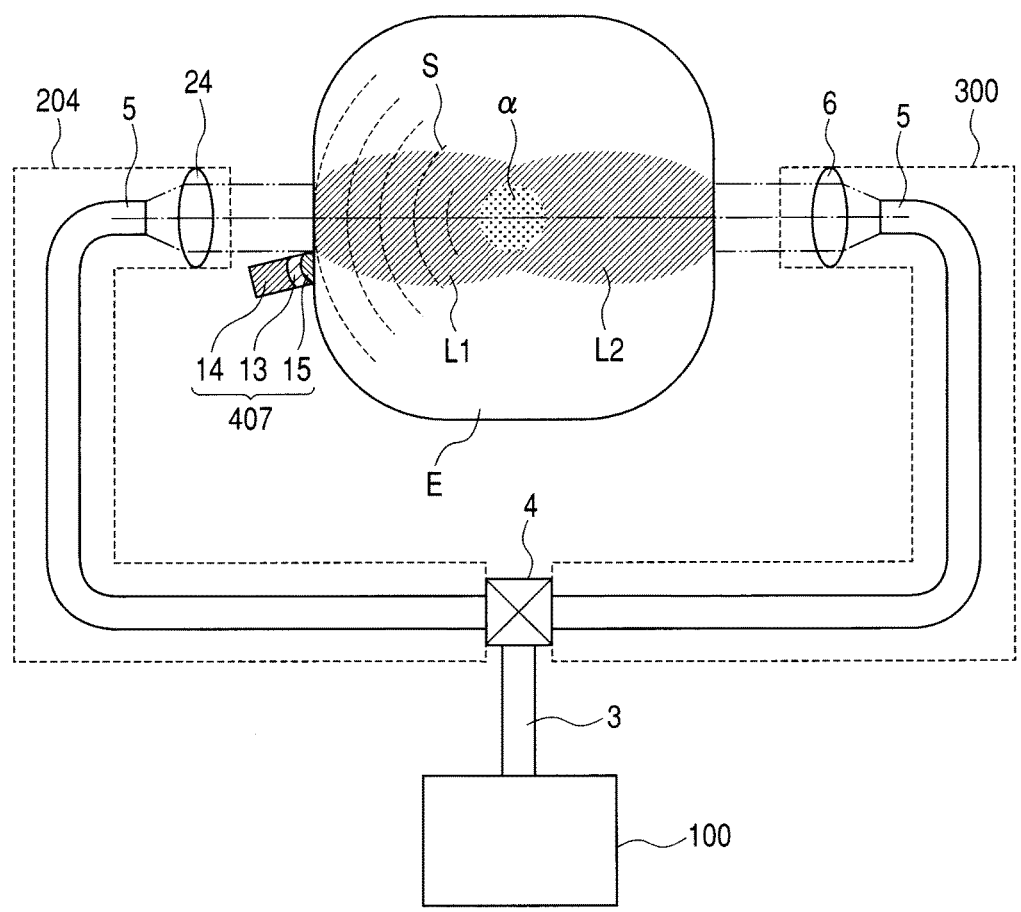
FIG. 13 is a diagram illustrating another structural example of the first illumination optical system and the ultrasonic detector according to Example 1 of the present invention.

As illustrated in FIG. 13, an ultrasonic detector 407 may be disposed at a position that does not interfere with a light path on the same side as that of the first illumination optical system 204 and is in a vicinity of the light path so that the signal can be detected with higher contrast than the conventional examples. In this case too, it can be said that the detection surface of the ultrasonic detector is positioned on the same side as that of the irradiation surface of the first illumination optical system 200.

Further, this example exemplifies the spectral analyzing method utilizing characteristics of the absorption spectrums of the oxyhemoglobin and the reduced hemoglobin as an example of using a wavelength in a range from 600 to 1,500 nm, but this example should not be interpreted as a limitation.

For instance, it is also possible to perform the spectral analysis with respect to water, fat, protein (collagen), and the like that are main structural materials of a biological tissue.

As described above, according to the measurement apparatus of Example 1, the first illumination optical system 200 and the second illumination optical system 300 are disposed to be opposed to each other via the inspection object disposed therebetween. Further, the center axes of axial symmetry of the regions illuminated by the illumination optical systems coincide with each other, and the ultrasonic detector 400 is disposed on the same surface as the irradiation surface of the first illumination optical system 200. In other words, the detection surface of the ultrasonic detector 400 is positioned on the same side as that of the irradiation surface for the first illumination optical system 200 to irradiate the inspection object with the pulse beam, with respect to the inspection object.

According to this structure, the photoacoustic signal generated from a boundary of the absorber α existing in a deep part of a biological tissue can be detected as a high contrast signal.

Therefore, it is possible to provide a measurement apparatus capable of measuring a position and a size of an absorber α with high accuracy. As a matter of course, the ultrasonic detector 400 may be disposed not on the side of the first illumination optical system 200 but on the side of the second illumination optical system 300 in the example described above.

Example 2

Figure 14:
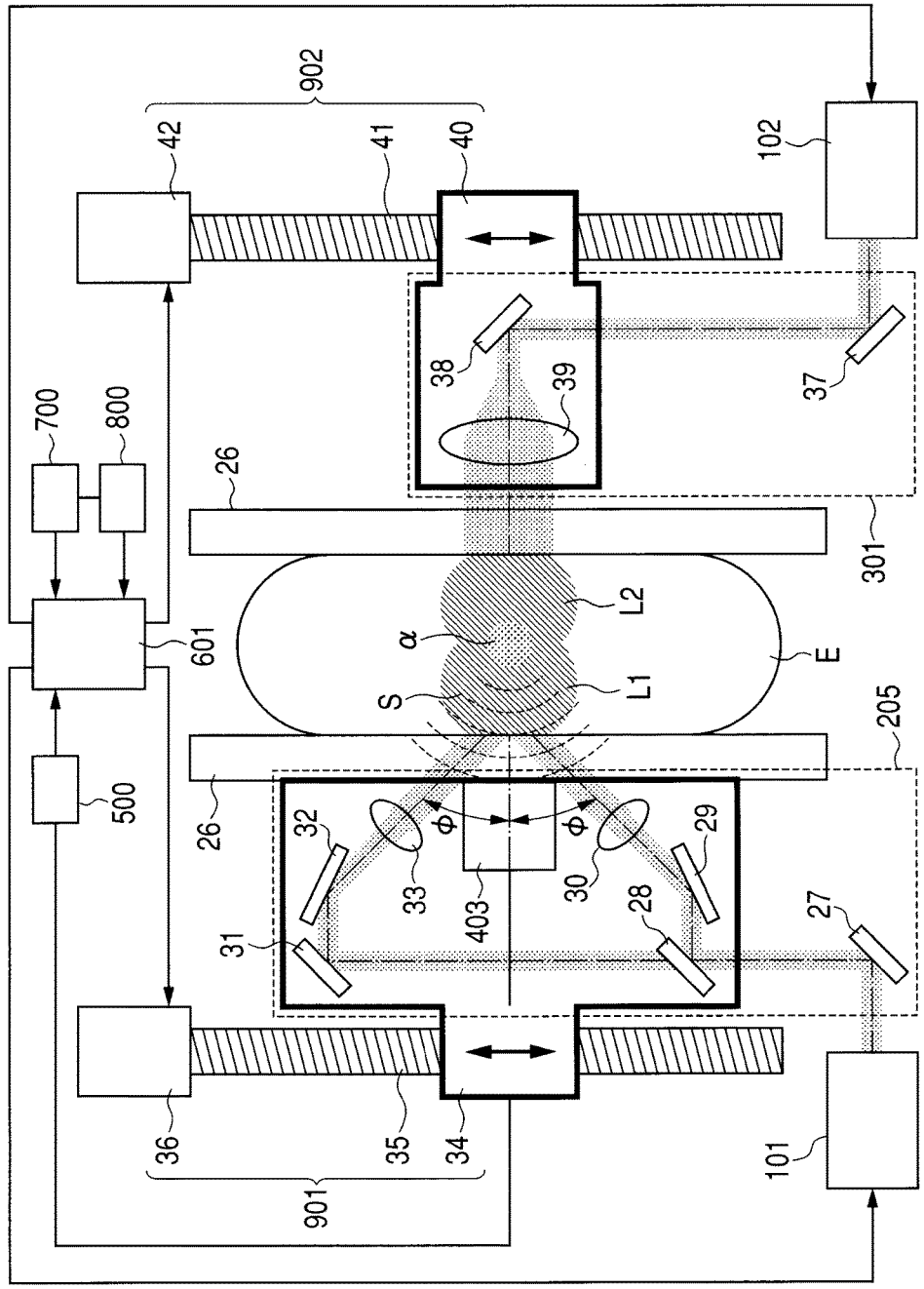
FIG. 14 is a diagram illustrating a schematic structure of a measurement apparatus according to Example 2 of the present invention.

In Example 2, a structural example of a measurement apparatus having a form different from that of Example 1 is described. FIG. 14 is a diagram illustrating a schematic structure of the measurement apparatus according to this example.

A basic structure of the measurement apparatus of this example is similar to the structure described above in Example 1, and a structural member denoted by the same numeral has the same function as that described above in Example 1.

In this example, a first drive mechanism 901 and a second drive mechanism 902 are newly disposed. The first drive mechanism 901 changes positions of a first illumination optical system 205 and the ultrasonic detector 403 with respect to the inspection object E. The second drive mechanism 902 changes a position of a second illumination optical system 301 with respect to the inspection object E.

Those drive mechanisms are controlled so that the individual structural members are scan-driven with respect to the inspection object E. Thus, the entire inspection object E can be measured.

The inspection object E is held between a first plate 25 and a second plate 26. The first plate 25 is a flat plate having a high transmittance property and a low attenuation property with respect to the light and the acoustic wave generated by the pulse beam generator 101.

A material constituting the first plate 25 can be similar to the material of the spacer 19 in Example 1.

The second plate 26 is a flat plate having a high transmittance property and a low attenuation property with respect to the light emitted from a pulse beam generator 102. A material constituting the second plate 26 can be similar to the material of the spacer 19, or glass or the like can be used.

The first illumination optical system 205 includes mirrors 27, 29, 31 and 32, a beam splitter 28, and lenses 30 and 33.

The pulse beam emitted from the pulse beam generator 101 is reflected by the mirror 27 and then divided into two beams by the beam splitter 28.

One of the divided beams is reflected by the mirror 29 and then enlarged by the lens 30 that is obliquely disposed at an angle φ with respect to the ultrasonic detector 403, so as to illuminate the surface of the inspection object E from one side of the ultrasonic detector 403.

The other divided beam is reflected by the mirrors 31 and 32, and then is enlarged by the lens 33 that is obliquely disposed at the angle φ in the opposite direction to the lens 30 with respect to the ultrasonic detector 403, so as to illuminate the surface of the inspection object E from the other side of the ultrasonic detector 403.

The first drive mechanism 901 includes a first slider 34, a first slide guide 35, and a first motor 36.

As an example of a member constituting the first slider 34 and the first slide guide 35, a ball screw, a linear guide or the like can be used.

The first slider 34 houses a set of the mirrors 29, 31 and 32, the beam splitter 28, the lenses 30 and 33, and the ultrasonic detector 403 of the first illumination optical system 205.

The set of members housed in the first slider 34 and the first slider 34 can be moved by the first slide guide 35 and the first motor 36 in a direction indicated by the arrow in FIG. 14.

Similarly to Example 1, the second illumination optical system 301 is disposed to be opposed to the first illumination optical system 205 via the inspection object disposed therebetween.

The second illumination optical system 301 includes mirrors 37 and 38, and a lens 39. The pulse beam emitted from the pulse beam generator 102 is reflected by the mirrors 37 and 38. Then, the pulse beam is enlarged by the lens 39 and is led to the surface of the inspection object E.

The second drive mechanism 902 includes a second slider 40, a second slide guide 41, and a second motor 42, for which members similar to the first drive mechanism 901 can be used.

The second slider 40 houses a set of the mirror 38 and the lens 39 of the second illumination optical system 301. The second slider 40 and the set of members housed in the second slider 40 can be driven by the second slide guide 41 and the second motor 42 in a direction indicated by the arrow in FIG. 14.

A controller 601 is connected to the pulse beam generators 101 and 102, the first drive mechanism 901, and the second drive mechanism 902.

In addition to the functions of the controller 600 described above in Example 1, the controller 601 controls positions, timings, and the like for driving the first drive mechanism 901 and the second drive mechanism 902.

The controller 601 drives and controls the positions so that the center axes of axial symmetry of the regions illuminated by the first illumination optical system 205 and the second illumination optical system 301 coincide with each other, and further controls so that the pulse beams are emitted simultaneously from the pulse beam generators 101 and 102.

The energies of light projected in this structure are combined in the inspection object E, and hence the energy fluence of light reaching a deep part of the inspection object E can be increased.

Next, the step of obtaining the spectral characteristic image of the inside of the tissue of the inspection object E by the measurement apparatus according to this example is described.

In the first step, the inspection object E is retained between the first plate 25 and the second plate 26. Then, a measurement start switch (not shown) is activated.

Next, in the second step, the pulse beam generators 101 and 102 are driven so as to emit pulse beams of the nanosecond order having a wavelength $\lambda 1 = 700$ nm.

Next, in the third step, the inspection object E is irradiated with the pulse beams by the first illumination optical system 205 and the second illumination optical system 301.

Next, in the fourth step, the photoacoustic signal S generated in the inspection object E is detected by the ultrasonic detector 403.

Next, in the fifth step, the signal analyzer 500 calculates a position and a size of the absorber α and the absorption coefficient μa based on the time characteristics of the detected photoacoustic signal S. The image in which the spatial distribution of the absorption coefficient μa of the absorber α and its periphery is reconstructed is generated.

Next, in the sixth step, the controller 601 stores the calculated position information of the absorption coefficient μa of the wavelength $\lambda 1$ and the image in the memory 700.

Next, in the seventh step, the controller 601 sets the wavelength of light emitted by the pulse beam generators 101 and 102 to be $\lambda 2 = 850$ nm, and the pulse beams of the nanosecond order having the wavelength $\lambda 2 = 850$ nm are emitted.

Next, in the eighth step, the steps similar to the third, fourth, and fifth steps described above are performed.

The controller 601 stores the calculated position information of the absorption coefficient μa of the wavelength $\lambda 2$ and the image in the memory 700.

Next, in the ninth step, the controller 601 drives the first drive mechanism 901 and the second drive mechanism 902 so that positions of the first slider 34 and the second slider 40 with respect to the inspection object E are changed to be the next measurement positions.

Next, in the tenth step, steps similar to the first, second, third, fourth, fifth, sixth, seventh, eighth, and ninth steps described above are performed until the measurement of every measurement positions are finished.

Next, in the eleventh step after all the measurement positions have been measured, the controller 601 superimposes the distribution images of the absorption coefficient μa having the wavelengths λ1 and λ2 and displays the result on the display 800.

Finally, in the twelfth step, the measurement is finished.

Figure 15:
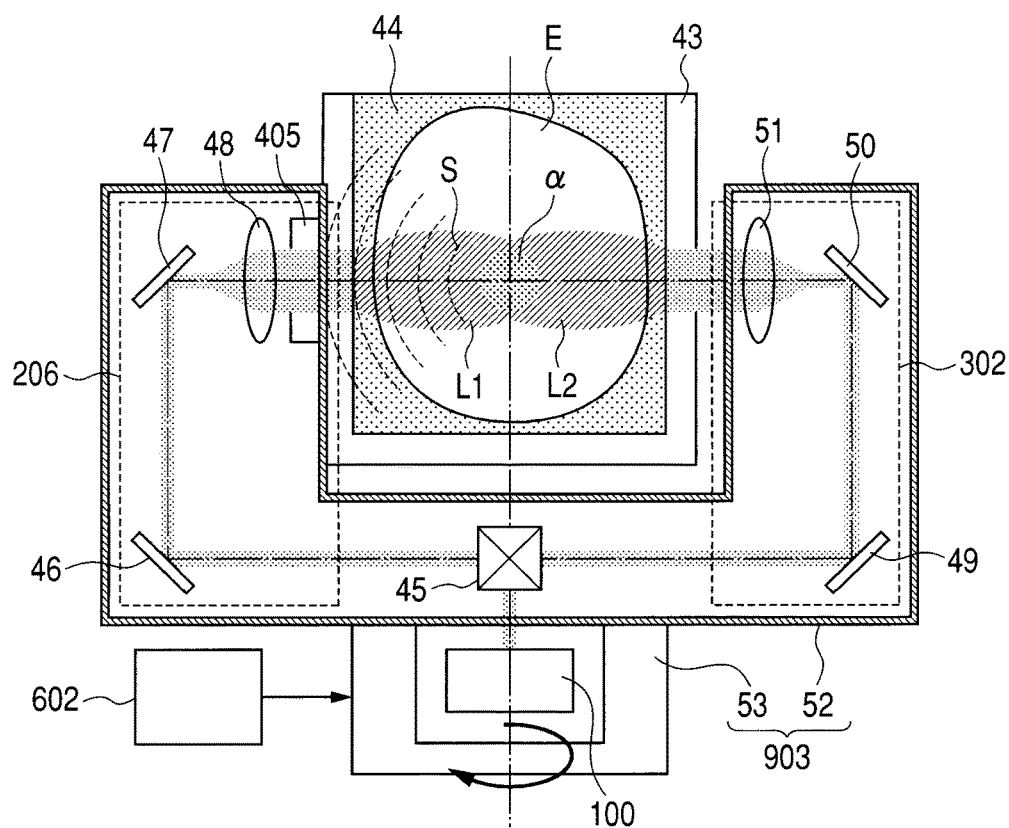
FIG. 15 is a diagram illustrating another structural example of the measurement apparatus according to Example 2 of the present invention.
Figure 16:
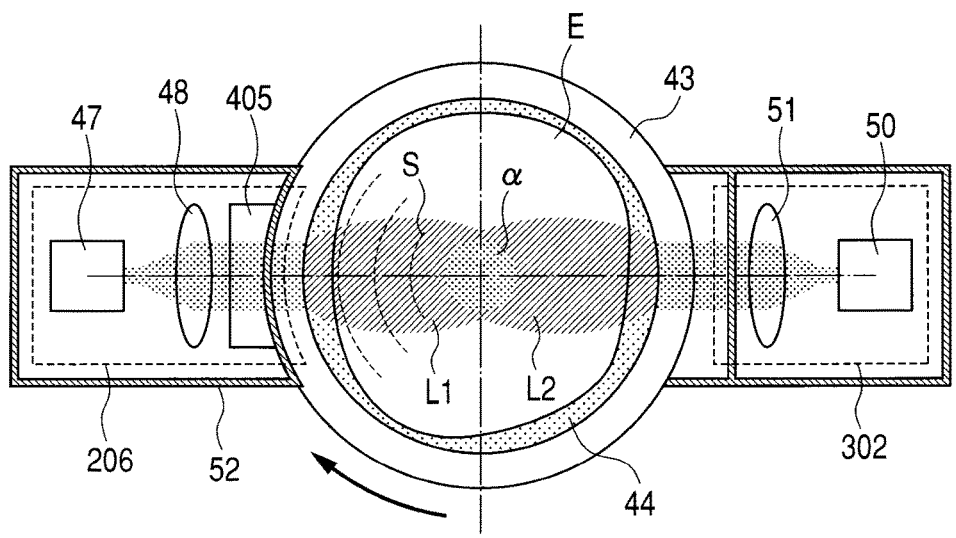
FIG. 16 is a diagram illustrating the another structural example of the measurement apparatus according to Example 2 of the present invention.

FIGS. 15 and 16 are schematic block diagrams of a measurement apparatus of another example according to Example 2. FIG. 15 is a side view, and FIG. 16 is an upper view.

A member denoted by the same reference symbol as that illustrated in FIGS. 1 to 14 is a member having the same function as described above.

In this example, a rotation drive mechanism 903 is disposed with respect to a cylindrical inspection object E. The rotation drive mechanism 903 changes positions of a first illumination optical system 206, the ultrasonic detector 405, and a second illumination optical system 302 with respect to the inspection object E.

The rotation drive mechanism 903 is controlled to conduct rotation scan-drive of the individual structural members with respect to the inspection object E, whereby the cylindrical inspection object E can be measured.

The inspection object E is held in a cylindrical housing 43. A matching agent 44 is filled in a gap between the inspection object E and the housing 43.

The housing 43 and the matching agent 44 have a high transmittance property and a low attenuation property with respect to light and an acoustic wave emitted by the pulse beam generator 100.

As a material constituting the housing 43, a material similar to the spacer 19 of Example 1 can be used. As a material constituting the matching agent 44, it is possible to use water, castor oil, ultrasonic inspection gel, or the like.

The first illumination optical system 206 includes mirrors 46 and 47, and a lens 48. A pulse beam emitted from the pulse beam generator 100 is divided into two beams by a beam splitter 45. One of the beams is led to the first illumination optical system 206, and the beam is reflected by the mirrors 46 and 47 and then is enlarged by the lens 48.

After that, the beam passes through the circular opening part of the ultrasonic detector 405 so as to illuminate the surface of the inspection object E via the housing 43 and the matching agent 44. The ultrasonic detector 405 is similar to the one described above with reference to FIG. 11.

Similarly to Example 1, the second illumination optical system 302 is disposed so as to be opposed to the first illumination optical system 206 via the inspection object disposed therebetween, and the center axes of axial symmetry of the regions illuminated by the illumination optical systems coincide with each other. In this example, the detection surface of the ultrasonic detector 405 is disposed on the same surface as the irradiation surface of the first illumination optical system 206 of the housing 43.

The second illumination optical system 302 includes mirrors 49 and 50, and a lens 51. The other of the two pulse beams divided by the beam splitter 45 is led to the second illumination optical system 302. The beam is reflected by the mirrors 49 and 50 and then is enlarged by the lens 51 so as to illuminate the surface of the inspection object E via the housing 43 and the matching agent 44.

The rotation drive mechanism 903 includes a rotation stage 52 and a motor 53 for driving the rotation stage 52. The rotation stage 52 houses a set of the beam splitter 45, the first illumination optical system 206, the ultrasonic detector 405, and the second illumination optical system 302.

The rotation stage 52 and the set of members housed in the rotation stage 52 can be driven by the motor 53 to rotate in a direction of the arrow illustrated in FIG. 15 or 16.

In addition to the functions of the controller 601 described above, a controller 602 controls positions, timings, and the like for driving the rotation drive mechanism 903, and is connected to the rotation drive mechanism 903.

As described above, according to the measurement apparatus of Example 2, the first illumination optical system and the second illumination optical system are disposed to be opposed to each other via the inspection object disposed therebetween. In addition, the center axes of axial symmetry of the regions illuminated by the illumination optical systems coincide with each other, and the detection surface of the ultrasonic detector is disposed on the same surface as the irradiation surface on the housing by the first illumination optical system. In other words, the detection surface of the ultrasonic detector is positioned on the same side as that of the irradiation surface for the first illumination optical system to irradiate the inspection object with the pulse beam, with respect to the inspection object.

The scan-drive of the individual structural members is performed with respect to the inspection object E while keeping the position relationship as described above, whereby a photoacoustic signal generated from a boundary of the absorber α existing in a deep part of the inspection object E can be detected as a high contrast signal in the entire inspection object E.

Therefore, it is possible to provide the measurement apparatus capable of measuring a position and a size of the absorber α with high accuracy.

Example 3

Figure 17:
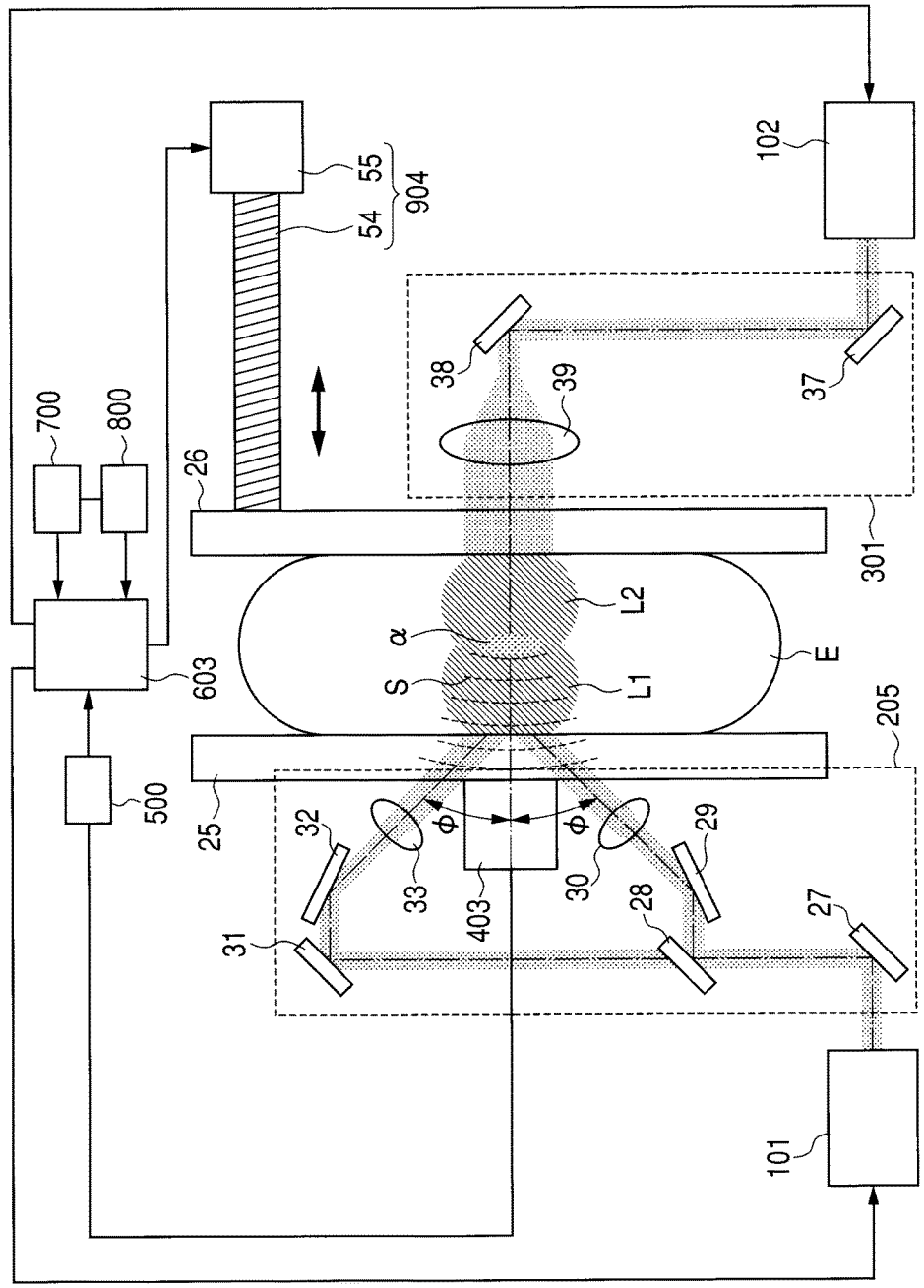
FIG. 17 is a diagram illustrating a schematic structure of a measurement apparatus according to Example 3 of the present invention.

FIG. 17 is a schematic block diagram of a measurement apparatus according to Example 3 to which the present invention can be applied.

The basic structure of the measurement apparatus is similar to the structure of Example 2 illustrated in FIG. 14, and structural members denoted by the reference symbols have the same function as those described above in Example 2.

In this example, a plate drive mechanism 904 is disposed additionally.

The plate drive mechanism 904 includes a slide guide 54 and a motor 55.

One end of the slide guide 54 is coupled to the second plate 26 contacting with the inspection object E, and the position of the second plate 26 can be moved in the arrow illustrated in FIG. 17. As an example of the member forming the slide guide 55, it is possible to use a ball screw, a linear guide, or the like.

Energy intensity of the light applied to the inspection object E is attenuated largely by influences of absorption and dispersion in the biological tissue, whereby measurement in a deep part is difficult.

Therefore, as to an inspection object such as a breast, it is considered to press the inspection object so as to increase the energy of light reaching the inside of the inspection object.

In this example, there is provided a function of controlling the plate drive mechanism 904 to press the inspection object E held between the first plate 25 and the second plate 26.

The second illumination optical system 301 is disposed so that the second illumination optical system 301 is opposed to the first illumination optical system 205, and that the center axes of axial symmetry of the regions illuminated by the second illumination optical system 301 and the first illumination optical system 205 coincide with each other.

The detection surface of the ultrasonic detector 403 is disposed on the same surface of the irradiation surface of the first illumination optical system 205 on the first plate 25.

In addition to the functions of the controller 601 of Example 2 described above, the controller 603 controls, for example, a position for driving the plate drive mechanism 904.

When this device presses the inspection object E, the spherical absorber α positioned in the inspection object E is deformed to be flat in the pressing direction.

Intensity of the photoacoustic signal S generated from the absorber α deformed in this manner has an anisotropy, and thus the stronger signal is generated from a flat region.

Therefore, the ultrasonic detector 403 is disposed on the same surface as that of the first illumination optical system 205 of the first plate 25 pressing the inspection object E so that the stronger photoacoustic signal S is detected.

As described above, in the measurement apparatus according to Example 3, the first illumination optical system and the second illumination optical system that press and illuminate the inspection object are disposed so that the first illumination optical system and the second illumination optical system are opposed to each other via the inspection object disposed therebetween, and that the center axes of axial symmetry of the regions illuminated by the first illumination optical system and the second illumination optical system coincide with each other.

In addition, the detection surface of the ultrasonic detector is disposed on the same surface of the irradiation surface (on the plate) of the first illumination optical system. In other words, the detection surface of the ultrasonic detector is positioned on the same side as that of the irradiation surface on which the first illumination optical system irradiates the inspection object with the pulse beam with respect to the inspection object. With the above-mentioned structure, a photoacoustic signal generated from a boundary of the absorber α positioned in a deep part of a biological tissue can be detected with a high contrast signal.

Therefore, it is possible to provide a measurement apparatus capable of measuring a position and a size of the absorber α with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-182060, filed Jul. 11, 2008, which is hereby incorporated by reference in its entirety.

The invention claimed is:

1. A measurement apparatus, comprising:
a light source configured to emit pulsed light of a particular wavelength;
an optical system having a pair of optical irradiation ends each of which is optically coupling with the light source and configured to irradiate an inspection object with the pulsed light;
an acoustic detection unit comprising a transducer and configured to face the inspection object to detect an acoustic wave generated in the inspection object and propagated from the inspection object and to convert the acoustic wave into an electric signal; and
a driving mechanism configured to move the pair of optical irradiation ends and the acoustic detection unit with respect to the inspection object simultaneously,
wherein the pair of optical irradiation ends are configured to face each other when the inspection object is disposed therebetween so that the inspection object is irradiated with the pulsed light from both sides of the inspection object,
wherein the acoustic detection unit is disposed on the same side as one of the pair of optical irradiation ends,
wherein the driving mechanism moves the acoustic detection unit intermittently, and
wherein the acoustic detection unit detects a first acoustic wave generated by a first light irradiation in a first wavelength and a second acoustic wave generated by a second light irradiation in a second wavelength during a time period when the driving mechanism does not move the acoustic detection unit.

2. The measurement apparatus according to claim 1, wherein the acoustic detection unit is arranged on a same side as that of a first optical irradiation end, and wherein the first optical irradiation end and the acoustic detection unit are disposed so that a full width at half maximum of an irradiation light intensity distribution of axial symmetry of a region illuminated by the first optical irradiation end overlaps with a full width at half maximum of a region for detecting the acoustic wave by the acoustic detection unit.

3. The measurement apparatus according to claim 2, wherein the first optical irradiation end and a second optical irradiation end are disposed so that a full width at half maximum of an irradiation light intensity distribution of axial symmetry of a region irradiated by the first optical irradiation end overlaps with a full width at half maximum of an irradiation light intensity distribution of axial symmetry of a region irradiated by the second optical irradiation end.

4. The measurement apparatus according to claim 3, wherein the driving mechanism maintains a position relationship among the first optical irradiation end, the second optical irradiation end, and the acoustic detection unit.

5. The measurement apparatus according to claim 1, wherein at least one end of the pair of optical irradiation ends comprises an end of an optical fiber.

6. The measurement apparatus according to claim 5, wherein the light source includes a pulsed laser light source having a wavelength within a range of 600 to 1,500 nm, and the optical fiber guides the pulsed light from the pulsed laser light source to the inspection object.

7. The measurement apparatus according to claim 1, wherein the light source includes a first light source and a second light source, wherein the pair of optical irradiation ends comprises an end of a first optical fiber and an end of a second optical fiber, and wherein the first optical fiber leads the pulsed light from the first light source to the inspection object, and the second optical fiber leads the pulsed light from the second light source to the inspection object.

8. The measurement apparatus according to claim 1, wherein the acoustic detection unit detects the first acoustic wave and the second acoustic wave without separating the acoustic waves from each other, and wherein a signal analyzer is configured to generate an image of absorption characteristics in the inspection object without separating the first acoustic wave from the second acoustic wave.

9. The measurement apparatus according to claim 1, wherein the acoustic detection unit is arranged on a same side as that of a first optical irradiation end, and the first optical irradiation end further comprises two distinct ends that are configured to irradiate the inspection object from both sides of the acoustic detection unit from an oblique angle with respect to the acoustic detection unit.

10. The measurement apparatus according to claim 1, wherein the pair of optical irradiation ends and the acoustic detection unit are arranged such that a center axis of axial symmetry of a region in which one of the pair of optical irradiation ends irradiates the inspection object, a center axis of axial symmetry of a region in which the other of the pair of optical irradiation ends irradiates the inspection object, and a center axis of axial symmetry of a region in which the acoustic detection unit detects an acoustic signal coincide with each other.

11. The measurement apparatus according to claim 10, wherein each of a penetration depth of the irradiated light from the pair of optical irradiation ends is overlapped onto each other.

12. The measurement apparatus according to claim 1, wherein a time period during which one of the pair of optical irradiation ends irradiates the inspection object with the pulsed light overlaps with a time period during which the other of the pair of optical irradiation ends irradiates the inspection object with the pulsed light.

13. The measurement apparatus according to claim 1, wherein the pair of optical irradiation ends further includes a third optical irradiation end which is optically coupled to the light source and configured to irradiate the inspection object with the pulsed light emitted by the light source,
wherein the acoustic detection unit is disposed adjacent to only one of the pair of optical irradiation ends or adjacent to the third optical irradiation end, and
wherein the pair of optical irradiation ends and the third optical irradiation end are configured to face each other when the inspection object is disposed therebetween, and the inspection object is simultaneously irradiated with the pulsed light from the pair of optical irradiation ends and the third optical irradiation end at different angles with respect to the acoustic detection unit.

14. The measurement apparatus according to claim 1, wherein each of a penetration depth of the irradiated light from the pair of optical irradiation ends is overlapped onto each other.

15. The measurement apparatus according to claim 1, wherein the particular wavelength is a near infrared wavelength.

16. The measurement apparatus according to claim 1, wherein the driving mechanism includes a first driving mechanism configured to move the acoustic detection unit and one of the pair of optical irradiation ends and a second driving mechanism configured to move the other of the pair of optical irradiation ends.

17. The measurement apparatus according to claim 1, wherein the driving mechanism moves the acoustic detection unit when the acoustic detection unit is set not to detect the first acoustic wave and the second acoustic wave, and wherein the driving mechanism does not move the acoustic detection unit when the acoustic detection unit is set to detect the first acoustic wave or the second acoustic wave.

18. The measurement apparatus according to claim 1, further comprising;
a signal analyzer configured to reconstruct a spatial distribution of an absorption coefficient based on the electric signal and generate an image of an absorption characteristics in the inspection object,
wherein the signal analyzer generates a first image of an absorption characteristics associated with the first light irradiation and a second image of the absorption characteristics associated with the second light irradiation during a time period when the driving mechanism does not move the acoustic detection unit.

19. A spectral characteristic imaging method comprising the steps of:
arranging a pair of optical irradiation ends, that are included in an optical system optically connected a light source, and an acoustic detection unit with respect to a to an inspection object,
irradiating the inspection object with a first light in a first wavelength,
detecting, with the acoustic detection unit, a first acoustic wave generated by the irradiation with the first light and converting the detected first acoustic wave into a first electric signal,
irradiating the inspection object with a second light in a second wavelength different from the first wavelength after the detecting the first acoustic wave,
detecting, with the acoustic detection unit, a second acoustic wave generated by an irradiation with the second light and converting the detected second acoustic wave into a second electric signal, and
moving the pair of optical irradiation ends and the acoustic detection unit after the detecting the second acoustic wave,
wherein, in the arranging step, the pair of optical irradiation ends are arranged on opposite sides of the inspection object such that the pair of optical irradiation ends are facing each other; and
wherein, in the arranging step, the acoustic detection unit is arranged on a same side of the inspection object as one of the pair of optical irradiation ends.

20. The spectral characteristic imaging method according to claim 19, further comprising:
analyzing the first electric signal and generating a first image of absorption characteristics associated with the first light, and
analyzing the second electric signal and generating a second image of absorption characteristics associated with the second light,
wherein the moving step is performed after the analyzing and generating an image of the first and second electric signals.

* * * * *